US010363358B2

United States Patent
Carmel et al.

(10) Patent No.: US 10,363,358 B2
(45) Date of Patent: Jul. 30, 2019

(54) INFUSION CATHETER WITH GUIDEWIRE VALVING

(71) Applicant: A.V. MEDICAL TECHNOLOGIES, LTD., Tel Aviv (IL)

(72) Inventors: Ilan Carmel, Tel Mond (IL); Michael Gabriel Tal, Savyon (IL); Josef Shahrur, Pardes Hanna-karkur (IL)

(73) Assignee: A.V. Medical Technologies Ltd., Tel Aviv (IL)

( * ) Notice: Subject to any disclaimer, the term of this patent is extended or adjusted under 35 U.S.C. 154(b) by 26 days.

(21) Appl. No.: 14/760,774

(22) PCT Filed: Jan. 8, 2014

(86) PCT No.: PCT/US2014/010752
§ 371 (c)(1),
(2) Date: Jul. 14, 2015

(87) PCT Pub. No.: WO2014/113257
PCT Pub. Date: Jul. 24, 2014

(65) Prior Publication Data
US 2015/0359998 A1 Dec. 17, 2015

Related U.S. Application Data

(60) Provisional application No. 61/752,649, filed on Jan. 15, 2013.

(51) Int. Cl.
*A61M 25/09* (2006.01)
*A61M 25/10* (2013.01)
(Continued)

(52) U.S. Cl.
CPC ............ *A61M 5/14* (2013.01); *A61M 25/003* (2013.01); *A61M 25/008* (2013.01);
(Continued)

(58) Field of Classification Search
CPC ...... A61M 25/0075; A61M 2025/0079; A61M 25/0023; A61M 25/003;
(Continued)

(56) References Cited

U.S. PATENT DOCUMENTS 4,585,000 A  4/1986  Hershenson
4,794,928 A  1/1989  Kletschka
(Continued)

FOREIGN PATENT DOCUMENTS

EP  0770405 A2  5/1997
WO  94/02196 A1  2/1994
(Continued)

OTHER PUBLICATIONS

Jul. 30, 2014 International Search Report issued in International Application No. PCT/US2014/010752.
(Continued)

*Primary Examiner* — Jason E Flick
*Assistant Examiner* — Courtney B Fredrickson
(74) *Attorney, Agent, or Firm* — Veros Legal Solutions, LLP

(57) ABSTRACT

The present disclosure relates to a PTA (percutaneous transluminal angioplasty) balloon catheter, preferably high pressure type, optionally introducible as an over the wire catheter. The catheter possess the attribute of injecting fluid to the treated site through a dedicated opening proximal to the balloon member, for introduction of fluids such as contrast enhancing material and/or medication. In some embodiments, a single lumen is used, at least in part, both for fluids transfer and dispersion ("infusion") as well as for guide wire passage. In some such embodiments, a valve mechanism is used to sustain selective operability of the lumen so that (Continued)

fluids will disperse mostly or solely through the proximal dispersion opening rather than the guide wire distal exit opening.

19 Claims, 14 Drawing Sheets

(51) Int. Cl.
*A61M 5/14* (2006.01)
*A61M 25/00* (2006.01)

(52) U.S. Cl.
CPC .... *A61M 25/0052* (2013.01); *A61M 25/0075* (2013.01); *A61M 25/09041* (2013.01); *A61M 25/104* (2013.01); *A61M 2025/0018* (2013.01); *A61M 2025/0076* (2013.01); *A61M 2025/0079* (2013.01); *A61M 2025/0081* (2013.01); *A61M 2025/091* (2013.01); *A61M 2025/1052* (2013.01); *A61M 2210/12* (2013.01)

(58) Field of Classification Search
CPC .. A61M 2025/0035; A61M 2025/0037; A61M 25/09; A61M 2025/09008; A61M 2025/1052; A61M 25/01; A61M 25/0102; A61M 2025/0183; A61M 25/10; A61M 2025/0021; A61M 2025/0031; A61M 25/0032; A61M 2025/004; A61M 25/005; A61M 2025/0018; A61M 2025/0076; A61M 2025/0081; A61M 2025/0091; A61M 2210/12; A61M 25/0052; A61M 25/09041; A61M 25/104
See application file for complete search history.

(56) References Cited

U.S. PATENT DOCUMENTS

| | | | |
|---|---|---|---|
| 5,069,673 A | 12/1991 | Shwab | |
| 5,267,979 A | 12/1993 | Appling et al. | |
| 5,306,247 A | 4/1994 | Pfenninger | |
| 5,318,032 A | 6/1994 | Lonsbury et al. | |
| 5,368,567 A | 11/1994 | Lee | |
| 5,439,447 A | 8/1995 | Miraki | |
| 5,693,088 A | 12/1997 | Lazarus | |
| 5,836,967 A | 11/1998 | Schneider | |
| 5,908,407 A | 6/1999 | Frazee et al. | |
| 6,010,521 A | 1/2000 | Lee et al. | |
| 6,017,323 A | 1/2000 | Chee | |
| 6,022,336 A * | 2/2000 | Zadno-Azizi | A61B 17/22 604/101.05 |
| 6,051,020 A | 4/2000 | Goicoechea et al. | |
| 6,231,543 B1 * | 5/2001 | Hegde | A61M 25/10 604/96.01 |
| 6,440,097 B1 | 8/2002 | Kupiecki | |
| 6,485,500 B1 | 11/2002 | Kokish et al. | |
| 6,544,217 B1 | 4/2003 | Gulachenski | |
| 6,663,648 B1 | 12/2003 | Trotta | |
| 7,195,611 B1 | 3/2007 | Simpson et al. | |
| 7,873,404 B1 | 1/2011 | Patton | |
| 8,532,749 B1 | 9/2013 | Patton | |
| 2002/0143251 A1 | 10/2002 | Richardson et al. | |
| 2003/0204236 A1 | 10/2003 | Letort | |
| 2004/0068250 A1 | 4/2004 | Boutilette et al. | |
| 2004/0116832 A1 | 6/2004 | Friedrich et al. | |
| 2004/0122465 A1 | 6/2004 | McMurtry et al. | |
| 2006/0064058 A1 | 3/2006 | Coyle | |
| 2006/0253071 A1 * | 11/2006 | Zattera | A61M 29/02 604/96.01 |
| 2007/0060882 A1 | 3/2007 | Tal | |
| 2007/0129752 A1 | 6/2007 | Webler et al. | |
| 2008/0221550 A1 | 9/2008 | Lee | |
| 2009/0312827 A1 * | 12/2009 | Stapleton | A61M 25/0108 623/1.11 |
| 2010/0198186 A1 * | 8/2010 | Ackermann | A61M 25/0023 604/500 |
| 2010/0256506 A1 | 10/2010 | Mohl | |
| 2011/0270373 A1 | 11/2011 | Sampognaro et al. | |
| 2012/0110598 A1 | 5/2012 | Rastogi et al. | |
| 2012/0265135 A1 * | 10/2012 | Porter | A61M 25/10 604/103.05 |
| 2012/0265287 A1 | 10/2012 | Sharma et al. | |
| 2013/0172661 A1 * | 7/2013 | Farnan | A61M 1/3653 600/16 |
| 2014/0316263 A1 | 10/2014 | Murphy | |
| 2015/0209557 A1 | 7/2015 | Tal et al. | |

FOREIGN PATENT DOCUMENTS

| | | | | |
|---|---|---|---|---|
| WO | 9505862 A1 | 3/1995 | | |
| WO | 99/42059 A2 | 8/1999 | | |
| WO | 01/56645 A1 | 8/2001 | | |
| WO | 2012110598 A1 | 8/2012 | | |
| WO | WO-2012110598 A1 * | 8/2012 | ......... | A61M 25/003 |
| WO | 2014/009809 A1 | 1/2014 | | |
| WO | 2014009809 A1 | 1/2014 | | |
| WO | 2014113257 A2 | 7/2014 | | |

OTHER PUBLICATIONS

Dec. 12, 2013 International Search Report issued in International Patent Application No. PCT/IB2013/001895.
Apr. 22, 2015 International Search Report issued in International Patent Application No. PCT/IB2015/000010.
Oct. 13, 2016 International Search Report for International Patent Application No. PCT/IB2016/053804.
Besarab et al. "Catheter Management in Hemodialysis Patients: Delivering Adequate Flow". Clinical Journal of the American Society of Nephrology. vol. 6 (2011): 227-234.
Hacker et al "Fibrin Sheath Angioplasty: A Technique to Prevent Superior Vena Cava Stenosis Secondary to Dialysis Catheters". The International Journal of Angiology: Official Publication of the International College of Angiology, Inc. 21-3 (2012): 129-134.

* cited by examiner

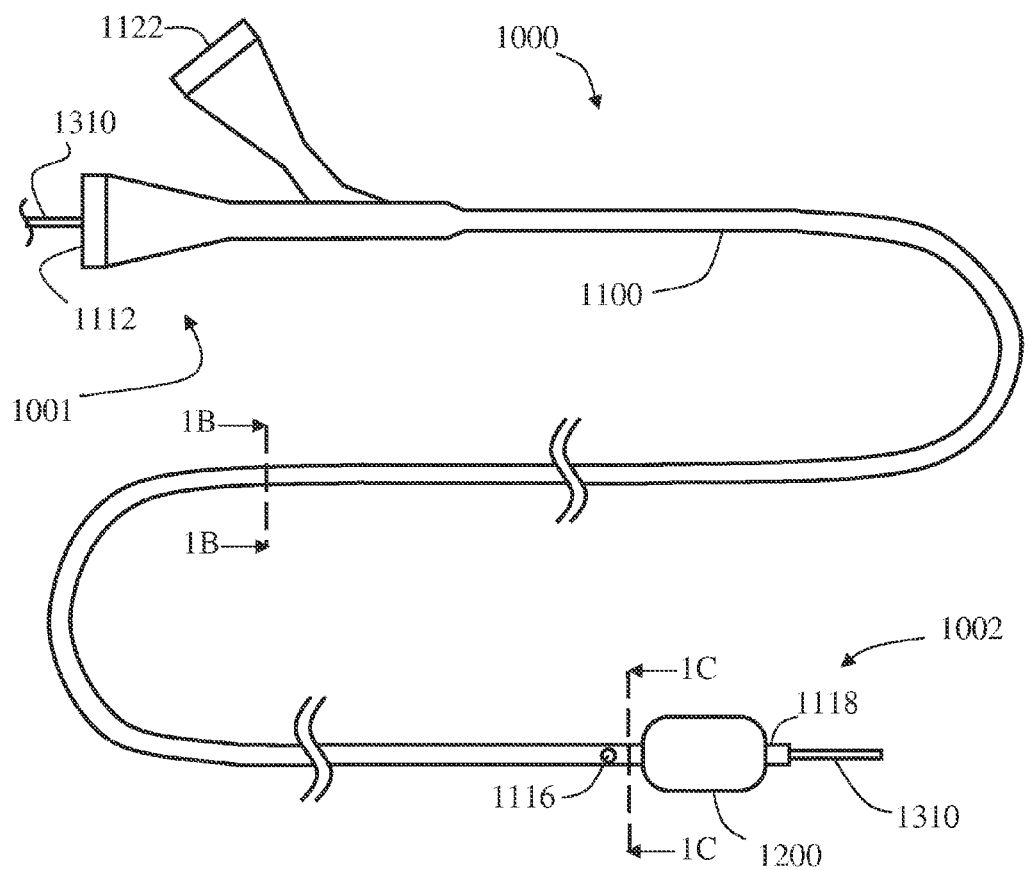
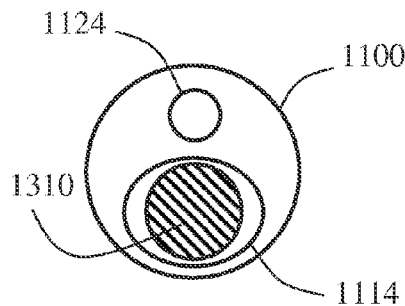 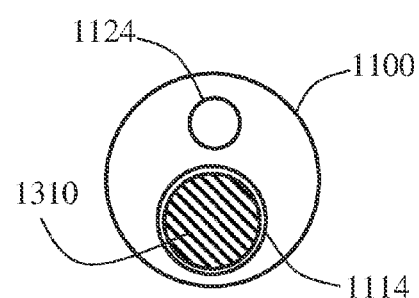
FIG 1A
FIG 1B　　FIG 1C

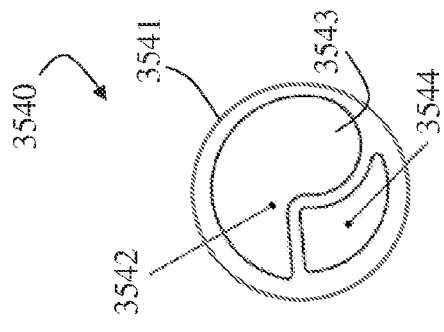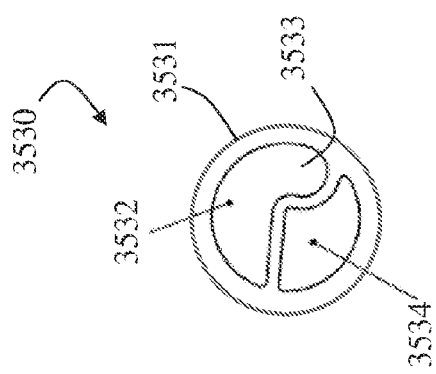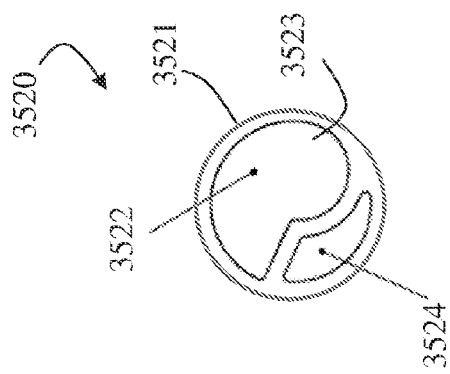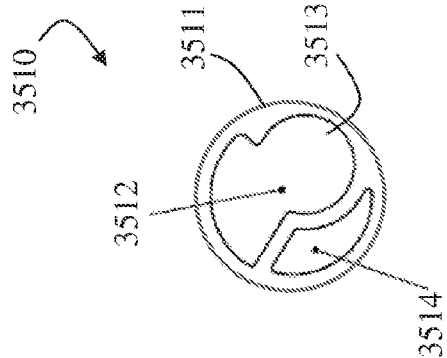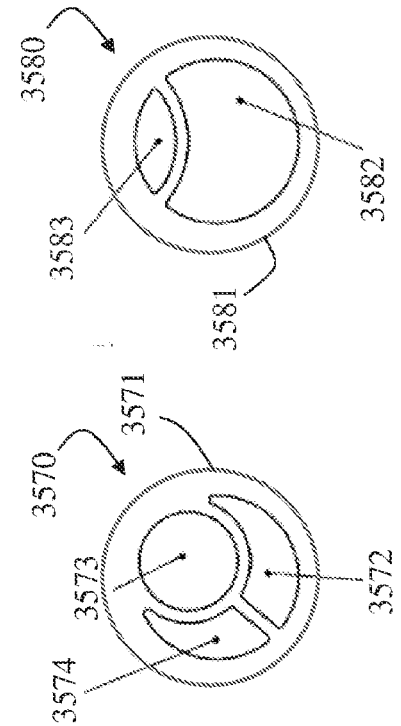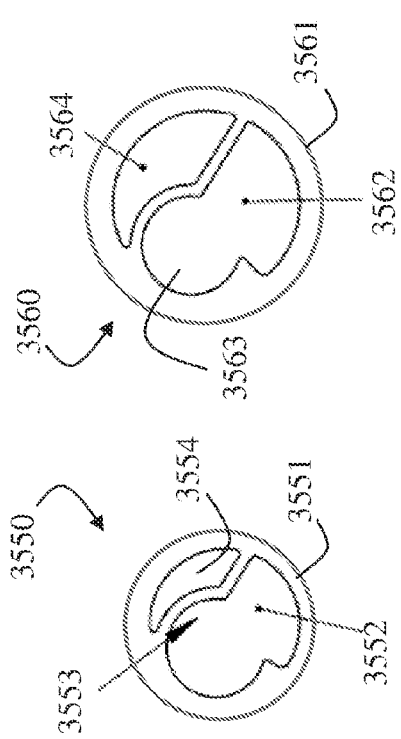

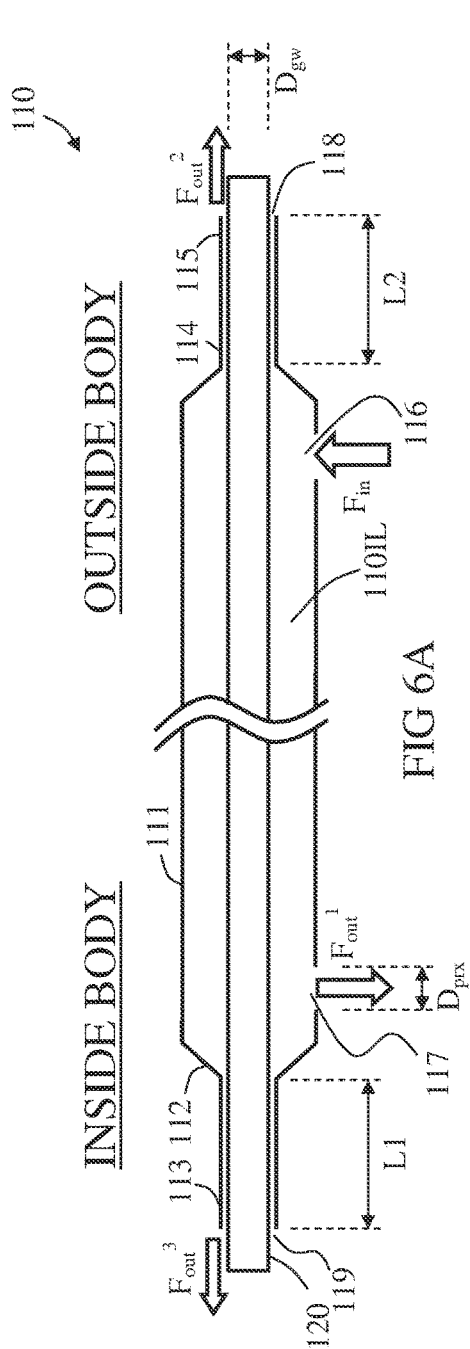
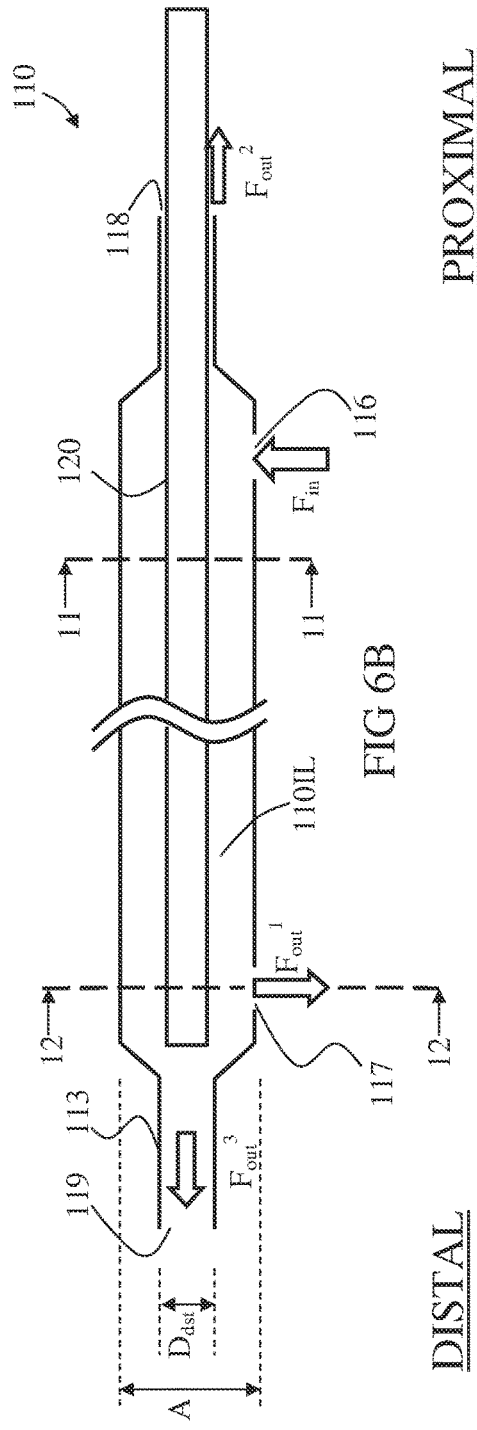
FIG 6A
FIG 6B

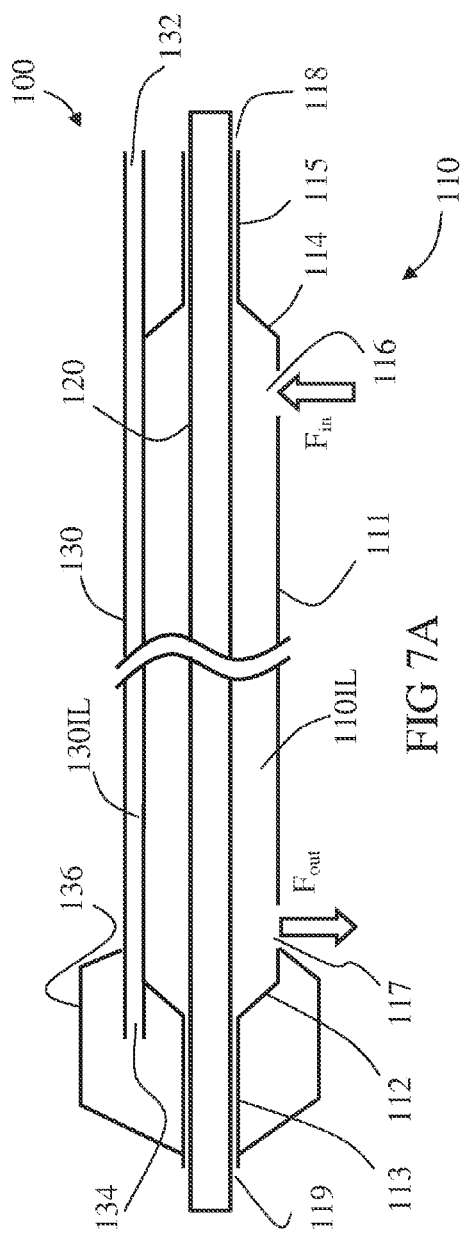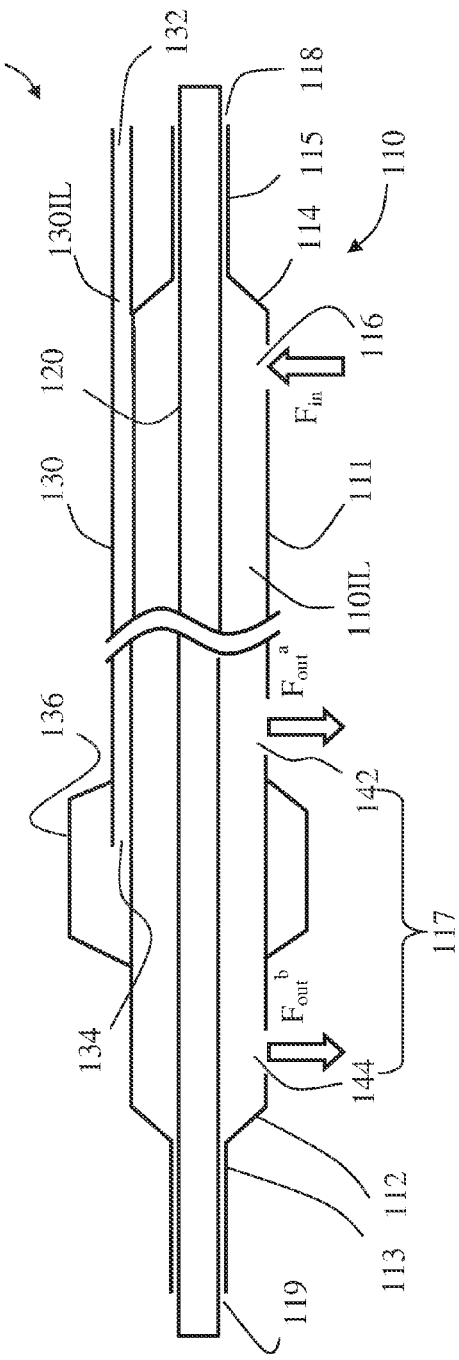

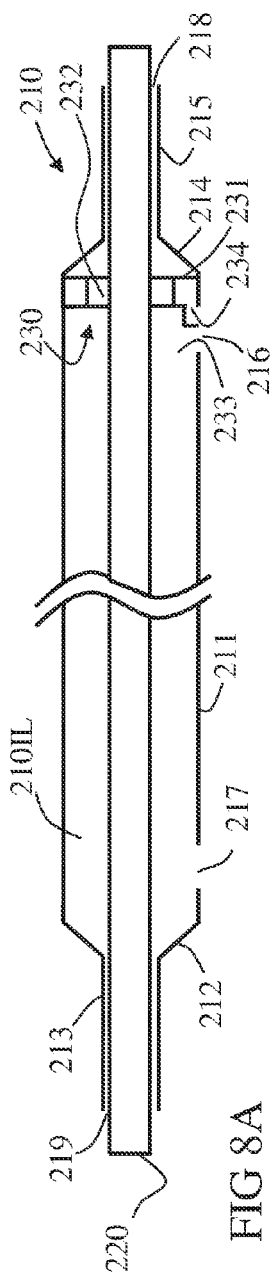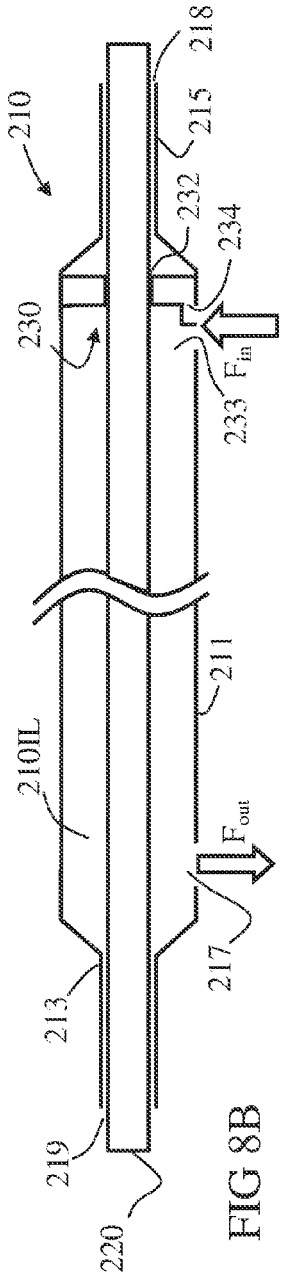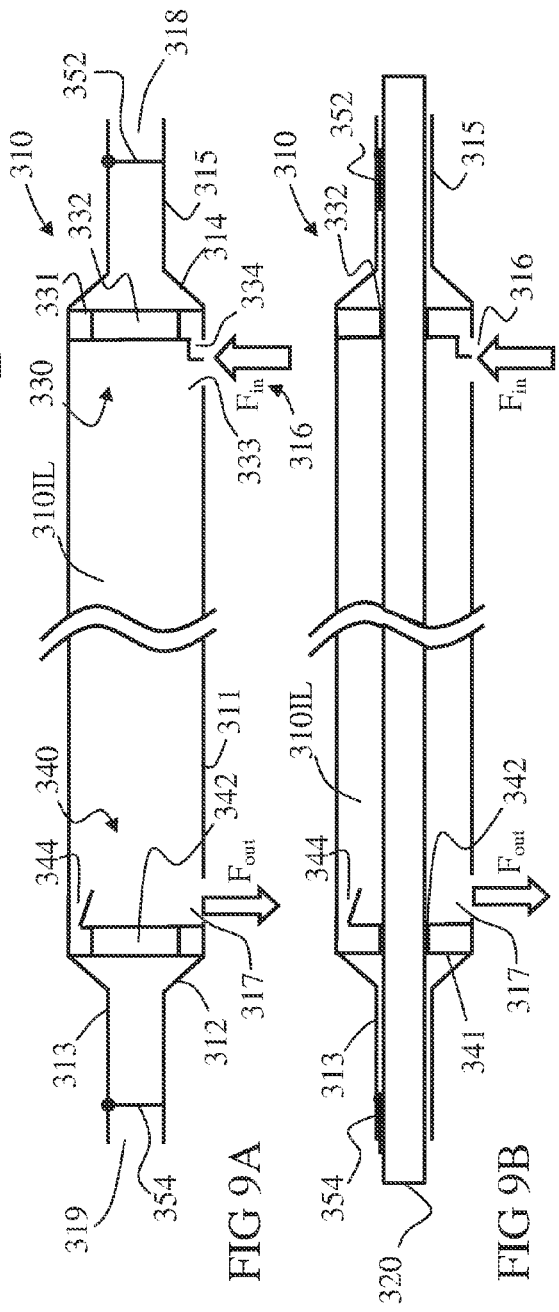
FIG 8A  FIG 8B  FIG 9A  FIG 9B

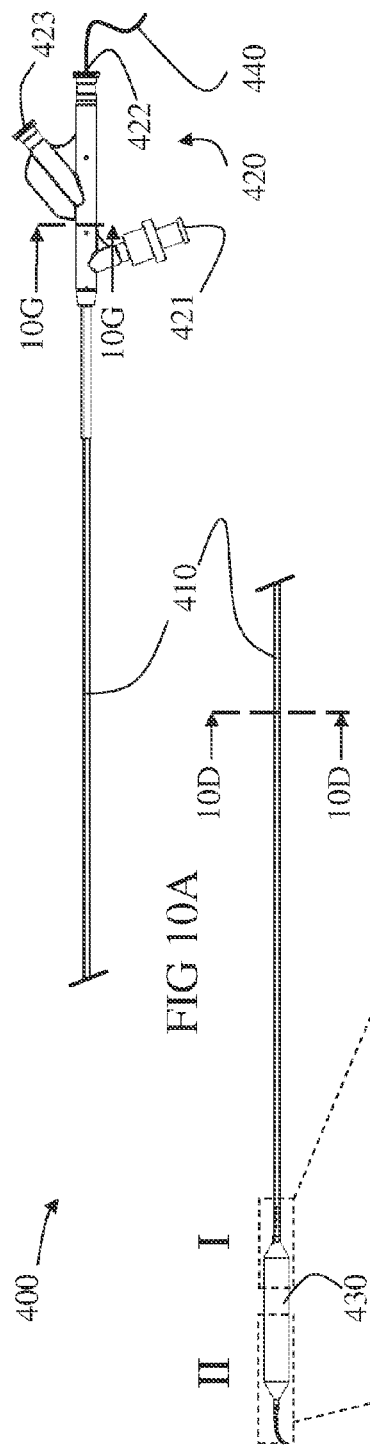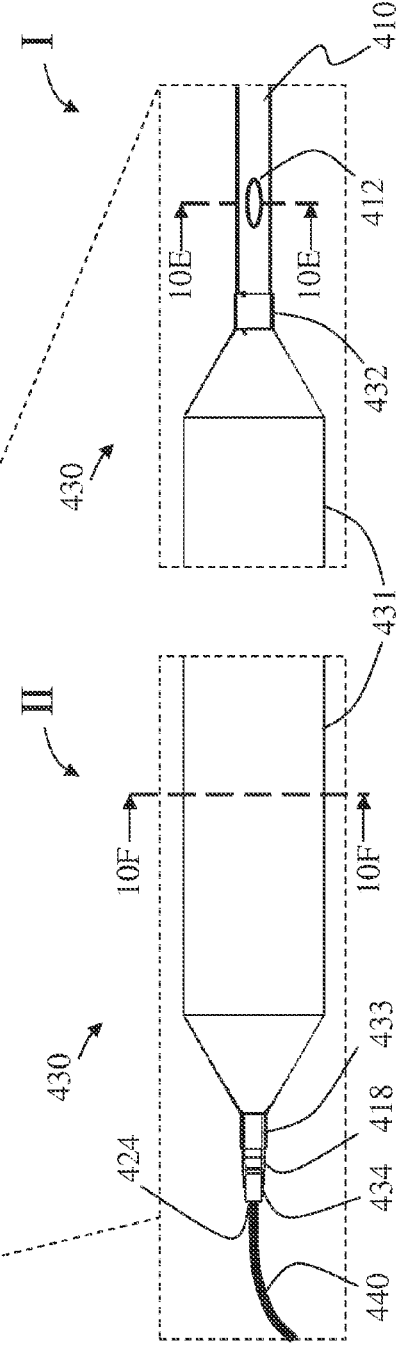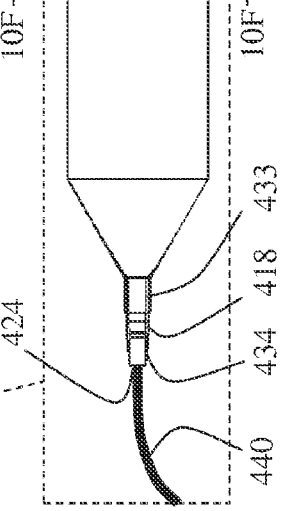
FIG 10A
FIG 10B
FIG 10C

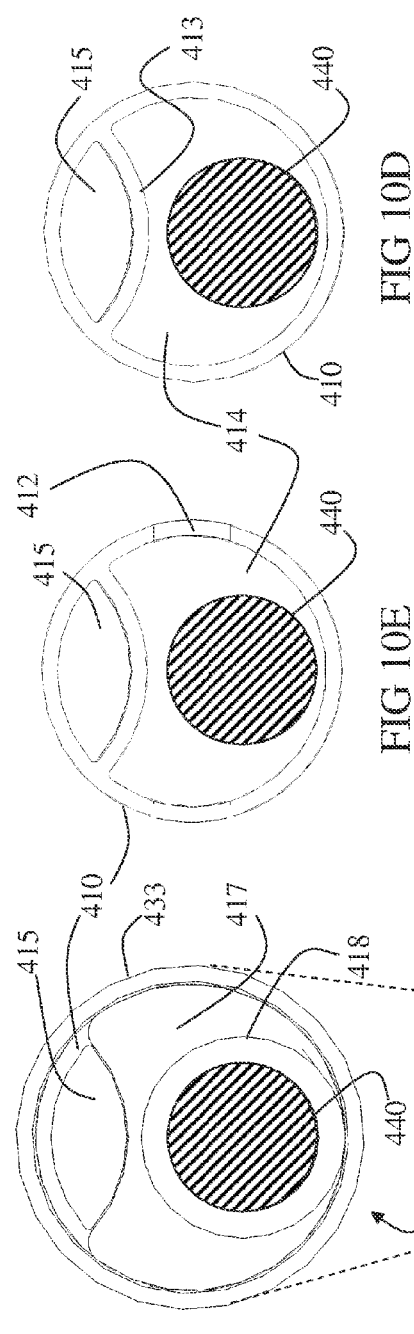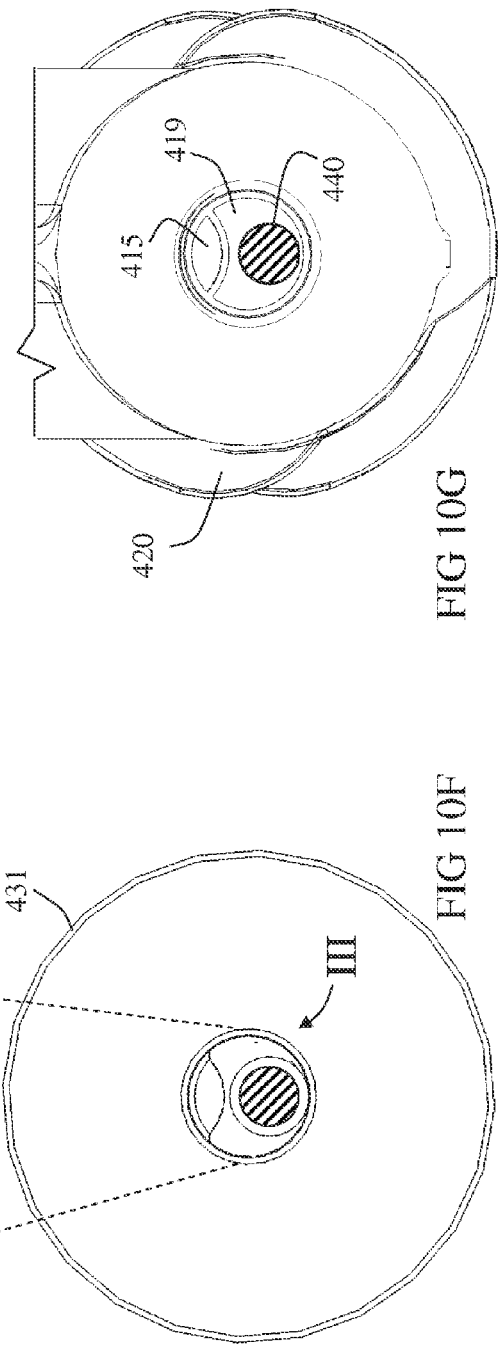

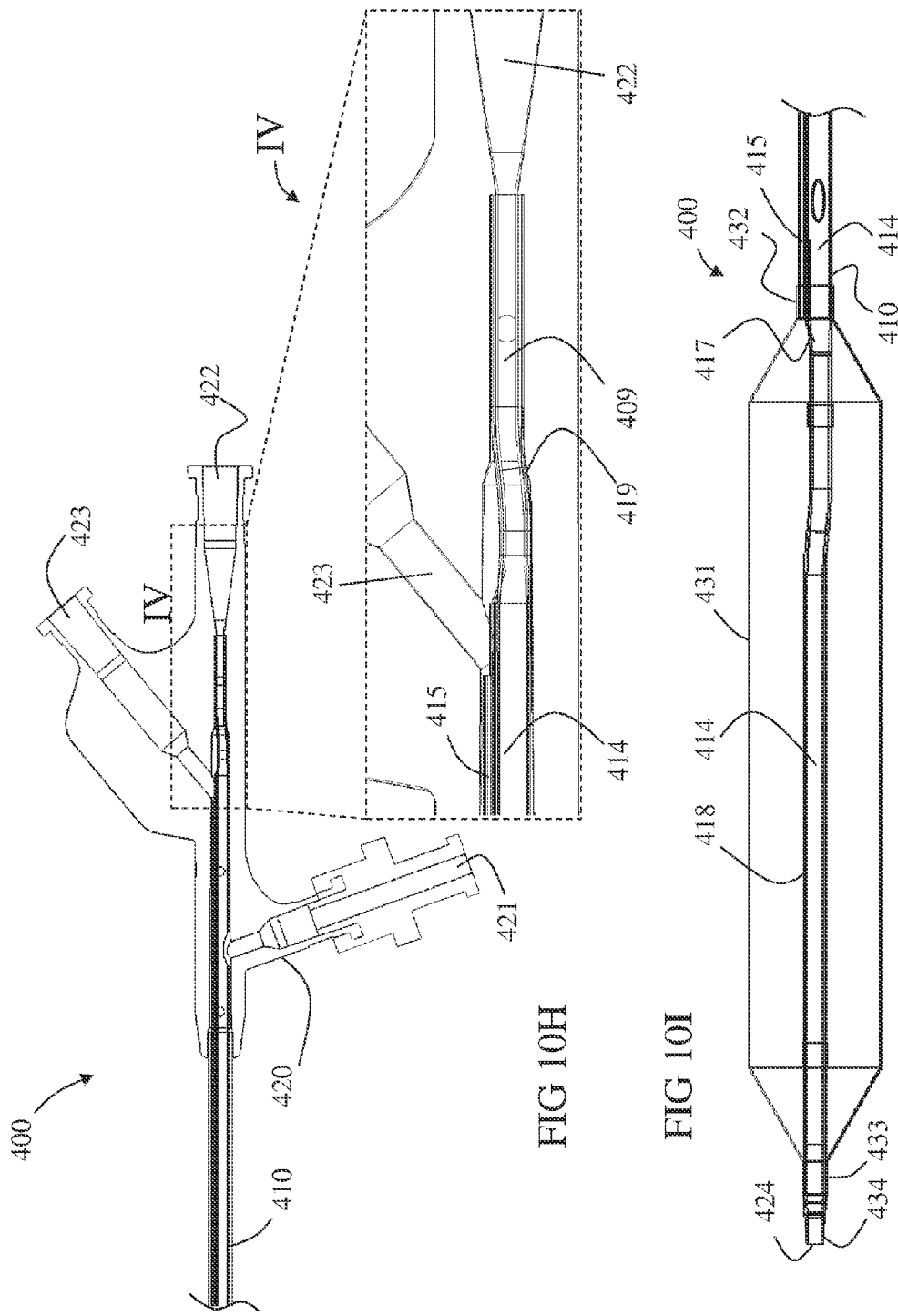

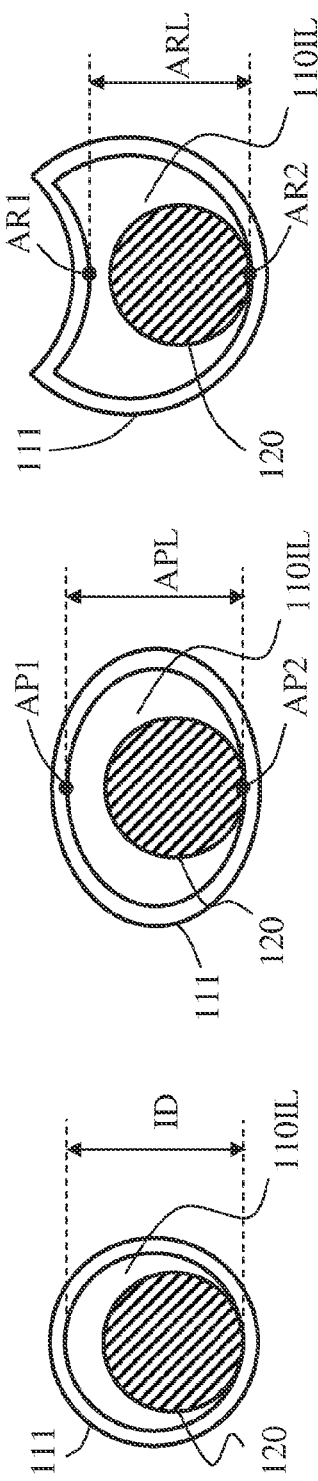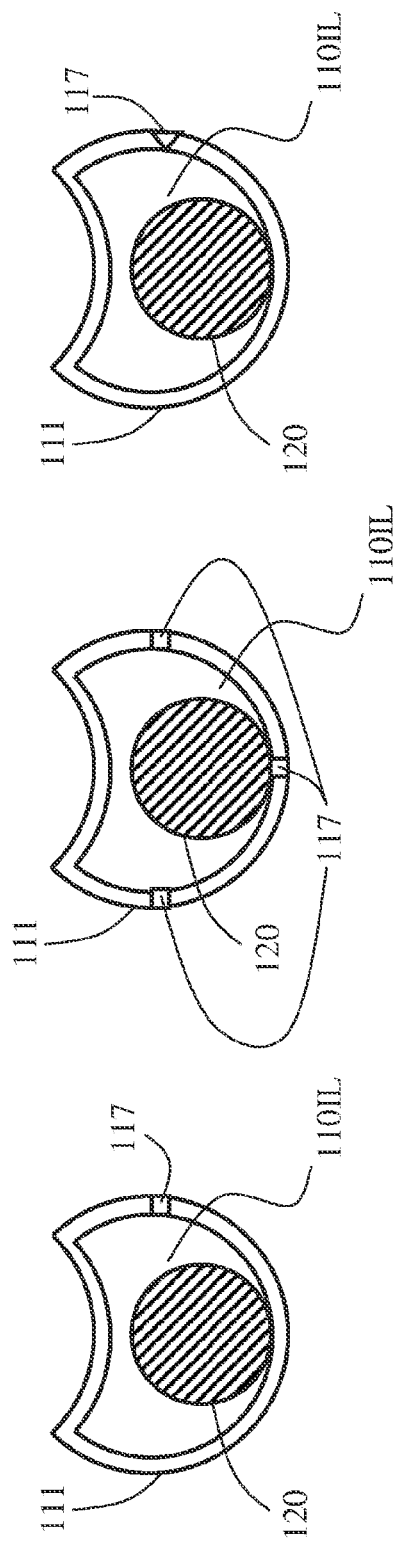

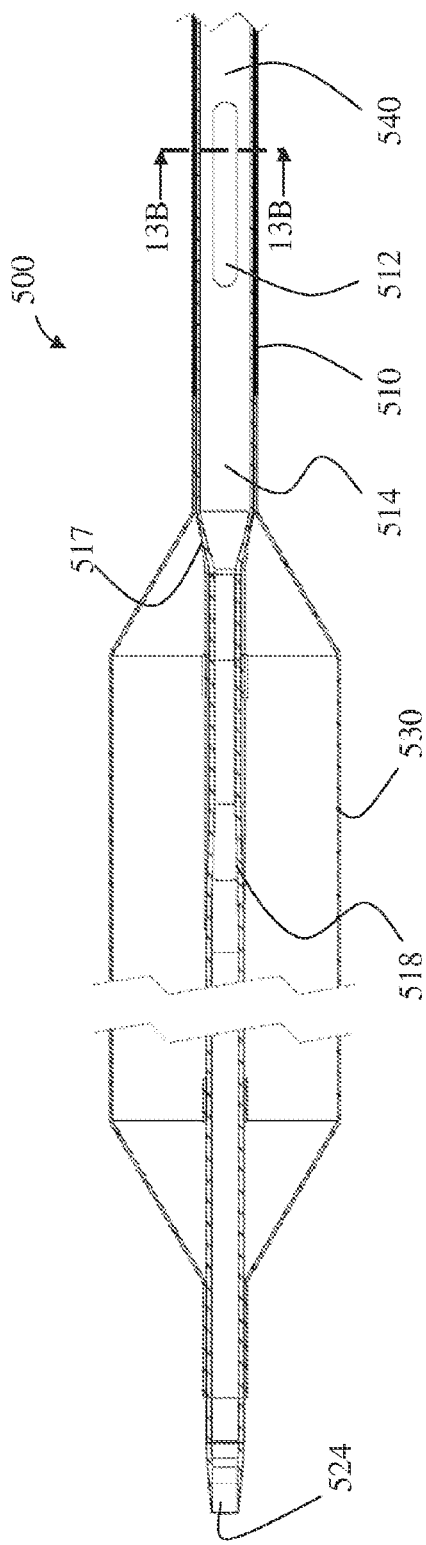
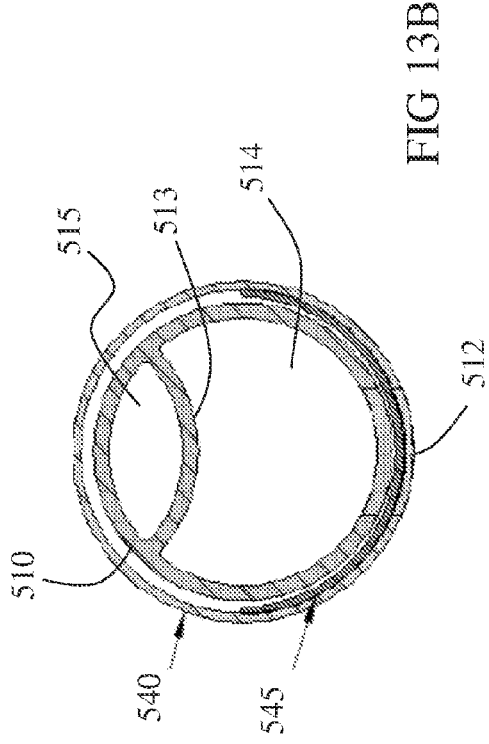
FIG 13A
FIG 13B

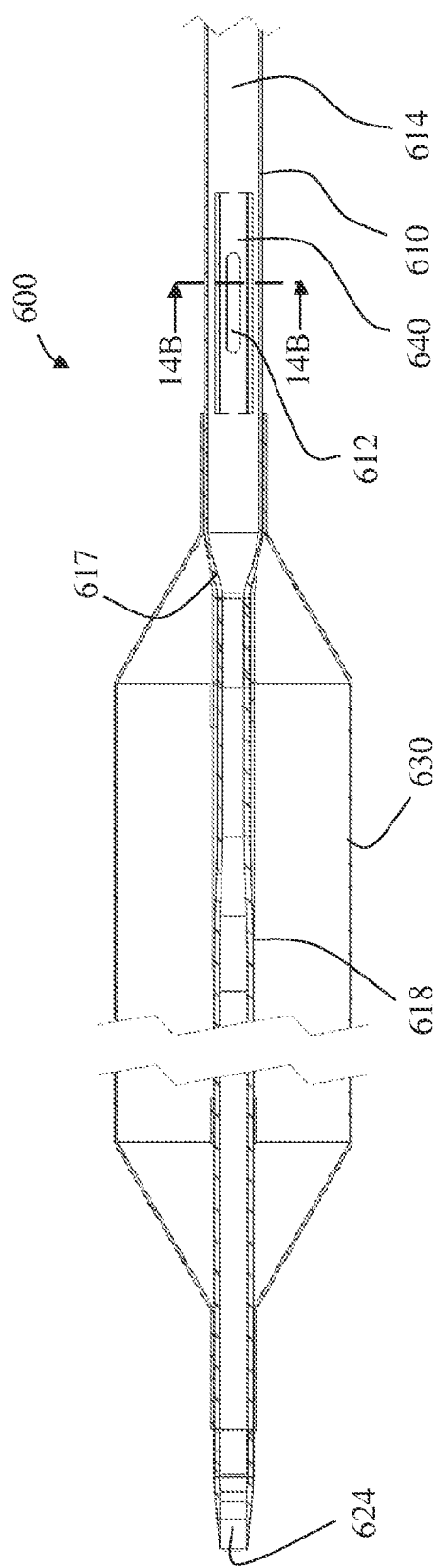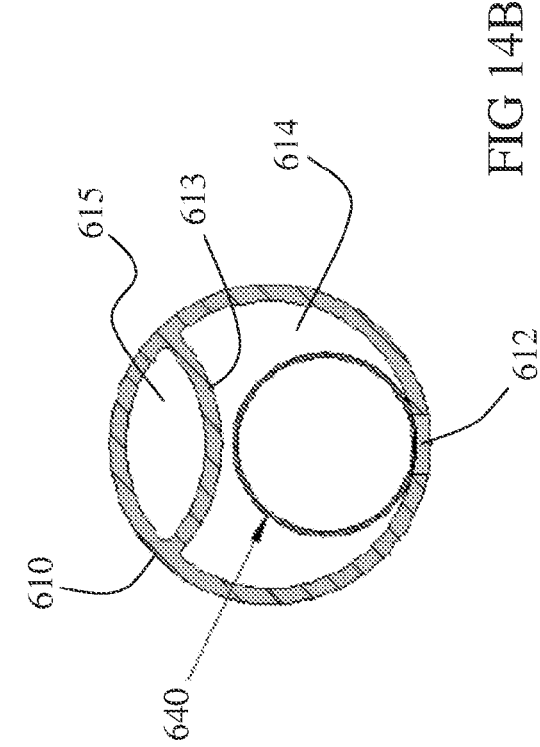
FIG 14A
FIG 14B

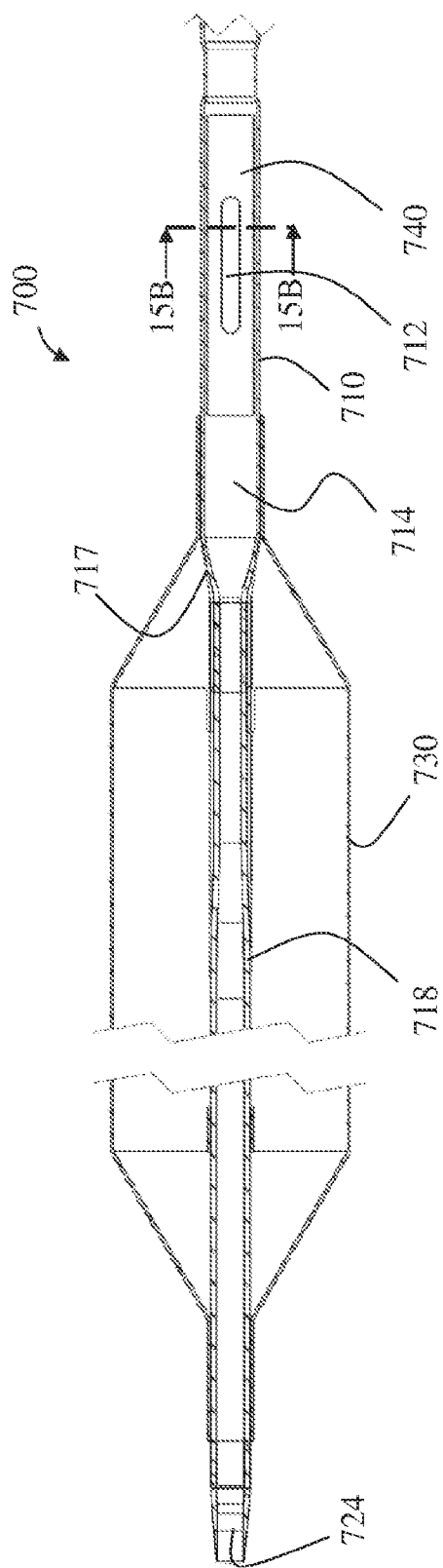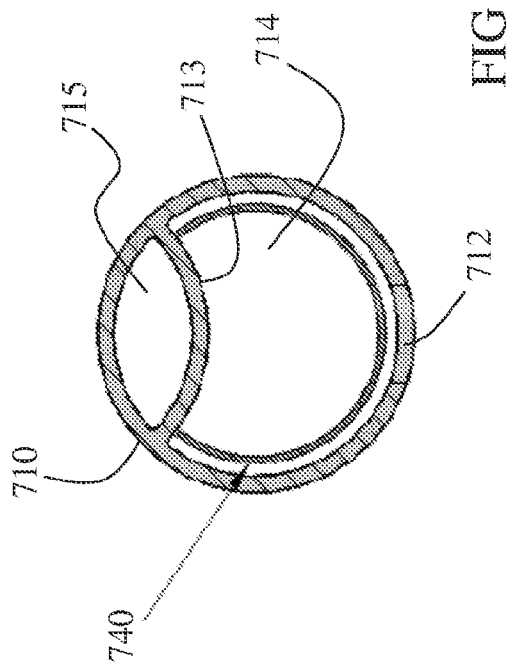
FIG 15A
FIG 15B

INFUSION CATHETER WITH GUIDEWIRE VALVING

CROSS REFERENCE TO RELATED APPLICATIONS

This application is a National Phase of PCT Patent Application No. PCT/US2014/010752, having International filing date of Jan. 08, 2014, which claims the benefit of priority under 35 U.S.C. § 119(e) of U.S. Provisional Application 61/752,649 filed on Jan. 15, 2013. The contents of the above applications are all incorporated by reference as if fully set forth herein in their entirety.

FIELD AND BACKGROUND OF THE INVENTION

The present invention, in some embodiments thereof, relates to medical devices, and in particular to balloon catheters applicable for treating blood vessels.

Balloon catheters are well known and used in treating various conditions in blood vessels. Two main types of balloon catheters in that area are dilatation balloon catheter, used to treat narrowed or stenotic portions of the vessel and recover flow (e.g., angioplasty balloon catheters), and occlusion balloon catheters, used to temporarily block flow out of a vessel segment while infusing fluid (e.g., medicament, contrast enhancer or flushing material) therein.

Some balloon catheters have at least three parallel functions, including: balloon inflation, travel over a guide wire, and infusion or dispersion of fluids therethrough. Such balloon catheters often include at least three lumens passing there along, including an inflation lumen, a guidewire lumen and an infusion lumen, correspondingly. In some occasions it is suggested to treat a blood vessel with a balloon catheter comprising an infusion exit opening located proximally to the balloon member, particularly if the balloon member is used for occlusion at least partially during infusion. U.S. Pat. No. 7,182,755 describes a use of an occlusion balloon catheter with a proximal infusion opening for treating hemodialysis vascular access. U.S. Pat. No. 5,368,567 describes a dilatation balloon catheter with a proximal infusion opening. The disclosures of both patents are fully incorporated herein by reference.

In some such occasions, minimization of catheter's lumens cross-sections is advantageous. In one example, there may be a need for a small diameter catheter for intraluminal passage (e.g., 3 F to 5 F) so it is more complex to introduce three lumens. In a second example, there may be a need to fortify the catheter shaft for high pressure dilatations (as in vascular access recanalization in certain anatomies), so it may be advantageous to decrease overall lumens size in a certain shaft diameter.

SUMMARY OF THE INVENTION

The present disclosure relates to a PTA (percutaneous transluminal angioplasty) balloon catheter, preferably high pressure type, optionally introducible as an over the wire catheter. The catheter possess the attribute of injecting fluid to the treated site through a dedicated opening proximal to the balloon member, for introduction of fluids such as contrast enhancing material and/or medication. Fluid injection can be performed simultaneously while inflating or deflating the balloon, or while balloon is maintained inflated. Possibly, number of radiopaque markings (preferably two or more) is present to define the working length of the balloon and facilitate in balloon placement. In some embodiments, a single lumen is used, at least in part, both for fluids transfer and dispersion ("infusion") as well as for guide wire passage. In some such embodiments, a valve mechanism is used to sustain selective operability of the lumen so that fluids will disperse mostly or solely through the proximal dispersion opening rather than the guide wire distal exit opening. In one example, the catheter ends with a tip, optionally an atraumatic tip with a check-valve integrated inside the guide wire lumen distal to the injection opening to allow infusion of fluids with or without the guide wire. Such a device can be used for multiple functions in sequence and/or in parallel, such as: performing high-pressure angioplasty in native arteriovenous dialysis fistulae or synthetic grafts; perform balloon dilatation and simultaneous contrast material injection; using smaller amounts of contrast enhancing material; decreasing use of angiograms and radiation exposure to staff and patient.

Catheters according to the present disclosures may be used also for embolectomy and declotting procedures. A device according to the present invention may include, though not necessarily, a relatively soft and compliant balloon fixed at the distal tip. The catheter possess the attribute of injecting fluid to the treated site through a dedicated opening proximal to the balloon for introduction of fluids such as clot dissolving material (such as t-PA). Fluid injection can be performed simultaneously while inflating or deflating the balloon, or while balloon is maintained inflated. Such a device can be used for multiple functions in sequence and/or in parallel, such as: performing balloon occlusion (possibly following dilatation) and simultaneous clot dissolving fluid injection; reducing the risk of clot migration to the arterial side during thrombectomy procedure and injection of contrast to the clogged access; using smaller amounts of contrast enhancing material; decreasing use of angiograms and radiation exposure to staff and patient.

According to an aspect of some embodiments of the present invention there is provided a catheter comprising a shaft, having a length, a proximal end and a distal end, and a wall enclosing an infusion lumen extending along the length and opened at both proximal and distal ends with corresponding proximal opening and distal opening. The infusion lumen is further opened with a lateral infusion opening disposed in the wall between the proximal end and distal end. The catheter also includes an inflatable member connected to the shaft adjacent the distal end and distal to the lateral infusion opening, and an inflation lumen sealed to the infusion lumen, extending between a proximal inflation opening at the proximal end and a distal inflation port opened to an interior of the inflatable member. A valving mechanism is selectively operable to block the distal opening thereby allowing infusion exit mostly or solely through the lateral infusion opening rather than mostly or solely through the distal opening.

A method for operating the catheter includes at least one of the following steps (not necessarily in same order):
1. inserting a guidewire in a luminal vessel;
2. delivering the catheter in the luminal vessel over the guidewire to a chosen target;
3. inflating the inflatable member to occlude the luminal vessel at the target; and
4. infusing a fluid through the lateral infusion opening proximal to the inflatable member such that no fluid passes beyond the inflatable member.

In some embodiments, the infusing occurs while the inflatable member is filled. Optionally, the method comprises a step of deflating the inflatable member after the infusing. Optionally, inflating the balloon generates a dilatation force in a magnitude above a mechanical yield point of a stenotic blood vessel wall.

In an aspect of some embodiments according to the present invention, there is provided a catheter which comprises an infusion wall enclosing an infusion lumen. In some embodiments the infusion lumen extends axially along the infusion wall, and comprises a proximal wall segment, a distal wall segment and an intermediate wall segment extending therebetween. In some embodiments, the proximal wall segment comprises a proximal guidewire opening and the distal wall segment comprises a distal guidewire opening. In some embodiments, the intermediate wall segment adjoins the distal wall segment with a narrowing. In some embodiments, the intermediate wall segment includes a fluid inlet appositional to the proximal wall segment and a fluid outlet appositional to the distal wall segment. In some embodiments, the proximal wall segment adjoins the intermediate wall segment with a widening. The narrowing and/or widening may be gradual.

In some embodiments, the infusion lumen in distal wall segment is sized, shaped, and/or inner surface of the distal wall segment is textured, such, to build a distal pressure gradient allocating a distal flow rate through the distal guidewire opening being 40% or less a fluid outlet flow rate through the fluid outlet, optionally 20% or less, optionally 10% or less, optionally 5% or less, optionally 2% or less. In some embodiments, the infusion lumen in proximal wall segment is sized, shaped, and/or inner surface of the proximal wall segment is textured, such, to build a proximal pressure gradient allocating a negative flow rate through the proximal guidewire opening being 40% or less a fluid outlet flow rate through the fluid outlet, optionally 20% or less, optionally 10% or less, optionally 5% or less, optionally 2% or less.

Optionally, the distal wall segment and/or the proximal wall segment is unobstructed, such as with a wire passing therein. Optionally and alternatively, the distal wall segment and/or the proximal wall segment is obstructed, partially or fully, with a guidewire, optionally a 0.035" guidewire, or optionally with a 0.025" guidewire, or optionally a 0.018" guidewire, or optionally with a 0.014" guidewire, or any other size, higher, lower or of an intermediate size.

In some embodiments, a cross section area of the fluid outlet divided by a cross section area of the distal guidewire opening is at least 1.2, optionally at least 1.5, optionally at least 2, optionally at least 5, optionally at least 10, or higher, or lower, or intermediate. Optionally, the distal wall segment is at least 10 mm in length, optionally at least 20 mm, optionally at least 50 mm, optionally at least 100 mm, or higher, or lower, or intermediate. In some embodiments, the distal pressure gradient is determined according to an infusion fluid viscosity of at least 0.5 centipoises, optionally at least 0.65 centipoises, optionally at least 3 centipoises, optionally at least 8 centipoises, optionally at least 14 centipoises, or higher, or lower, or intermediate.

In some embodiments, a cross section area of the proximal guidewire opening is equal to or less than a cross section area of the distal guidewire opening. In some embodiments, a cross section of the infusion lumen in the distal wall segment and/or in the proximal wall segment is circular and 0.3 to 1.5 mm in diameter, optionally 0.9 to 1 mm in diameter, optionally 0.3 to 0.9 mm in diameter. In some embodiments, a cross section of the infusion lumen in the intermediate wall segment is noncircular shaped with a smallest distance between antipodal points at an inner boundary thereof being at least 0.5 mm. Optionally, a cross section of the infusion lumen in the intermediate wall segment is crescent shaped with a smallest distance between two opposing arcs at an inner boundary thereof being at least 0.5 mm. Optionally, a cross section area of the infusion lumen in the intermediate wall segment is at least 1.5 mm$^2$, optionally at least 1.75 mm$^2$, optionally at least 2 mm$^2$.

In some embodiments, the fluid outlet includes at least one opening such as a hole and/or at least one slit which may be configured to open above a predetermined infusion pressure of at least 1 bar, optionally of at least 2 bars.

In some embodiments, the catheter also includes an inflatable member and an inflation wall enclosing an inflation lumen, with the infusion wall, along a length thereof. The inflatable member may be a dilatation balloon comprising a non-compliant or a semi-compliant material, or, optionally and alternatively, a non-compliant material. In some embodiments, the inflatable member is provided in between the fluid outlet and the distal guidewire opening. Optionally ands alternatively, the fluid outlet includes a proximal-most opening and a distal-most opening, wherein the inflatable member extends therebetween.

In some embodiments, a guidewire seal is provided in the infusion lumen between the fluid inlet and the proximal guidewire opening and/or between the fluid outlet and the distal guidewire opening. Optionally, the guidewire seal allows a guidewire travel therethrough. Optionally, the guidewire seal is annular shaped and inflatable to decrease in inner diameter below to a predetermined guidewire diameter. Optionally, alternatively or additionally, a zero seal is provided between the fluid inlet and the proximal guidewire opening and/or between the fluid outlet and the distal guidewire opening. Optionally, the zero seal is normally closed to fluid flow at the absence of a guidewire passing therethrough.

In some embodiments, the fluid outlet includes a single opening with a total opened area being equal to or greater than the cross section area of infusion lumen proximal to the fluid outlet less a cross section area of a guidewire with a minimal prescribed diameter. Optionally, a structural fortification is added to the infusion wall about the opening. Optionally, the fortification includes a mesh patch, a tube insert or a sheet insert.

In one specific implementation, a catheter has an infusion wall enclosing an infusion lumen extending axially therealong. The infusion lumen includes three segments: a proximal wall segment, a distal wall segment and an intermediate wall segment extending therebetween. The proximal wall segment comprises a proximal guidewire opening and the distal wall segment comprises a distal guidewire opening so that a guidewire may be positioned within the infusion lumen. The intermediate wall segment adjoins the distal wall segment with a narrowing such that the distal wall segment has a smaller minimal cross sectional area than a minimal cross sectional area of said intermediate wall segment. When a guidewire is positioned in the infusion lumen, it fits tighter in the distal wall segment of the infusion lumen than it does in the larger intermediate wall segment. The narrowed distal wall segment is narrowed for a length of at least 20 mm. This effectively seals the distal end of the catheter, while at the same time allowing fluid to relatively freely migrate from a fluid inlet in the intermediate wall segment, around the guidewire in the intermediate wall segment, and out of a fluid outlet in the intermediate wall segment. In some embodiments, the cross sectional area of the fluid outlet is equal to or greater than the minimal cross sectional area of the intermediate wall segment minus the minimal cross sectional area of the distal wall segment. In some embodiments, a similar at least 20 mm length of narrowed portion of the infusion lumen is positioned on the proximal side of the catheter as well.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D schematically illustrate an exemplary balloon catheter comprising a combined infusion-guidewire lumen with selective valving mechanism, in accordance with embodiments of the present invention;

FIGS. 5A-H schematically illustrate cross sections in portions of different exemplary catheters, in accordance with embodiments of the present invention;

FIGS. 6A-B schematically illustrate an exemplary infusion lumen comprising a first exemplary valving mechanism, in accordance with embodiments of the present invention;

FIGS. 7A-B schematically illustrate balloon catheter incorporating exemplary valving mechanisms differentiated by balloon location relative to fluid outlet, in accordance with embodiments of the present invention;

FIGS. 8A-B schematically illustrate an exemplary infusion lumen comprising an exemplary valving mechanism with an additional exemplary backflow seal, in accordance with embodiments of the present invention;

FIGS. 9A-B schematically illustrate an exemplary infusion lumen comprising an exemplary valving mechanism with additional exemplary proximal and distal sealing sets, in accordance with embodiments of the present invention;

FIGS. 10A-I illustrate side views and cross section views of an exemplary angioplasty infusion balloon catheter comprising a guidewire based valving mechanism, in accordance with embodiments of the present invention;

FIGS. 11A-C schematically illustrate different exemplary cross section shapes for an intermediate section of an infusion lumen, in accordance with embodiments of the present invention;

FIGS. 12A-C schematically illustrate different exemplary fluid outlet types and/or distribution, in accordance with embodiments of the present invention;

FIGS. 13A-B schematically illustrate cut views of an exemplary balloon catheter with a single proximal fluid outlet comprising a first exemplary fortification, in accordance with embodiments of the present invention;

FIGS. 14A-B schematically illustrate cut views of an exemplary balloon catheter with a single proximal fluid outlet comprising a second exemplary fortification, in accordance with embodiments of the present invention; and FIGS. 15A-B schematically illustrate cut views of an exemplary balloon catheter with a single proximal fluid outlet comprising a third exemplary fortification, in accordance with embodiments of the present invention.

DESCRIPTION OF EMBODIMENTS OF THE INVENTION

Figure 1D:
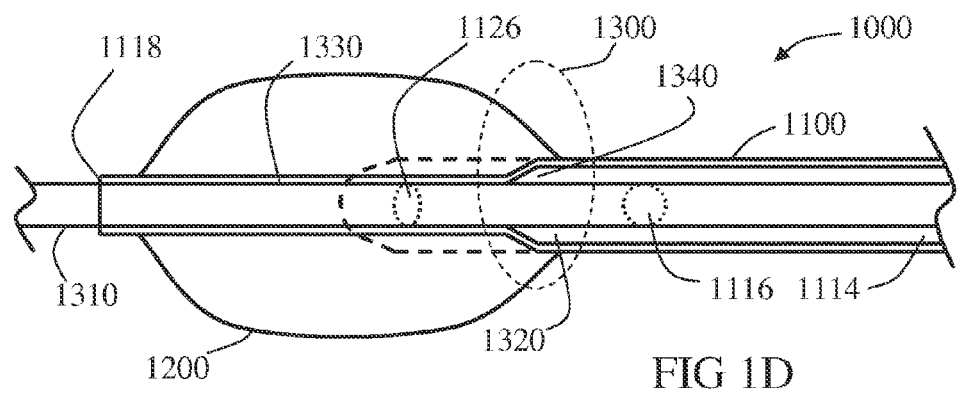

The following preferred embodiments may be described in the context of exemplary balloon catheters for treating blood vessels. However, the invention is not limited to the specifically described devices and methods, and may be adapted to various clinical applications without departing from the overall scope of the invention.

Referring to the drawings, FIGS. 1A-D schematically illustrate an exemplary balloon catheter 1000 comprising a combined infusion-guidewire lumen (referred to as infusion lumen 1114) with selective valving mechanism 1300. Catheter 1000 includes a shaft 1100 having a length, a proximal end 1001 and a distal end 1002, and a wall enclosing infusion lumen 1114 which is extending along shaft's 1100 length and opened at both proximal end 1001 and distal end 1002 with corresponding proximal opening 1112 and distal opening 1118. Infusion lumen 1114 is further opened with a lateral infusion opening 1116 (or optionally a number of openings) disposed in shaft's 1100 wall between proximal end 1001 and distal end 1002.

An inflatable member 1200 is connected to shaft 1100 adjacent its distal end, distal to lateral infusion opening 1116. An inflation lumen 1124, sealed to infusion lumen 1114, extends between a proximal inflation opening 1122, at shaft's 1100 proximal end, and a distal inflation port 1126, opened to an interior of inflatable member 1200. Inflatable member 1200 may be a compliant balloon, a semi-compliant balloon or a non-compliant balloon.

A valving mechanism according to the present disclosure may be any type of controller, such as a mechanical device, for selectively controlling a flow parameter of a fluid, for example a flow rate. A valving mechanism may be set between two or more modes that inhibit fluid flow by different amounts. In some cases, the modes may include a fully closed mode in which flow is substantially absent, and a fully opened valve in which fluid is allowed to travel substantially unhindered by the valving mechanism. Intermediate flow restrictions are also possible. According to some preferred embodiments of the present disclosure, a valving mechanism includes an elongated member such as a wire (e.g., a guide wire) operational to selectively pass through or withdraw from an infusion lumen portion sized and shaped substantially the same as external boundaries of a correlating portion thereof, being substantially narrowed as compared to a proximal portion of the infusion lumen located between a fluid inlet and a fluid outlet, such that when the wire occupies the narrowed infusion lumen portion then no flow or at least substantially no flow will pass therethrough. When the obstructing wire is fully withdrawn from the constricted or narrowed infusion lumen portion, fluid can pass therethrough. In an optional alternative embodiment, other valving means may be applied so that no fluid may pass through the narrowed infusion lumen portion also when the obstructing wire is absent, so that all or at least substantially all fluid will be delivered through a fluid outlet that is positioned proximal to the narrowed infusion lumen portion.

As shown in FIG. 1, guidewire-based valving mechanism 1300 may be provided in infusion lumen 1114 distal to lateral infusion opening 1116. Valving mechanism 1300 is selectively operable to block distal opening 1118 of infusion lumen 1114 such that fluid passing distally through infusion lumen 1114 shall exit mainly or solely through lateral infusion opening 1116 rather than through distal opening 1118. In case that valving mechanism 1300 is set not to block distal opening 1118, flow may pass via distal opening 1118 at all or in a greater rate.

As shown, infusion lumen 1114 defines a first segment 1320, extending between proximal opening 1112 and a boundary 1340 (shown adjacent to lateral infusion opening 1116 although it may be further distal), and a second segment 1330, extending between boundary 1340 and distal opening 1118. In some embodiments, in first segment 1320, infusion lumen 1114 has a first minimal cross section area, and in second segment 1330, infusion lumen 1114 has a second minimal cross section area smaller than the first minimal cross section than in first segment 1320. Valving mechanism 1300 includes an elongated member, preferably a guide wire 1310 selectively disposable in infusion lumen 1114 at first segment 1320 and/or second segment 1330. Guide wire 1310 is sized and configured to pass through proximal opening 1112, infusion lumen 1114 and/or distal opening 1118, and therefore allow an over-the-wire delivery of catheter 1000 thereupon. Optionally and alternatively, catheter 1000 is configures for rapid exchange deliveries.

Figure 4A:
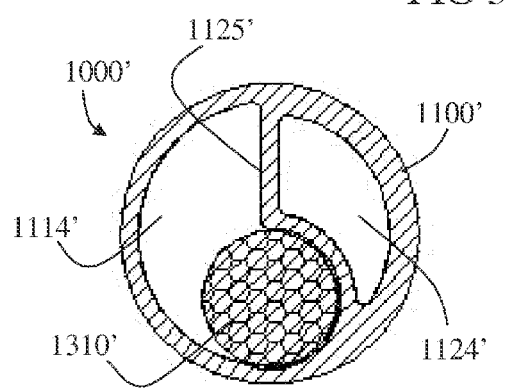
FIGS. 4A-B schematically illustrate cross sections in portions of two different exemplary catheters comprising combined infusion-guidewire lumen, in accordance with embodiments of the present invention.
Figure 4B:
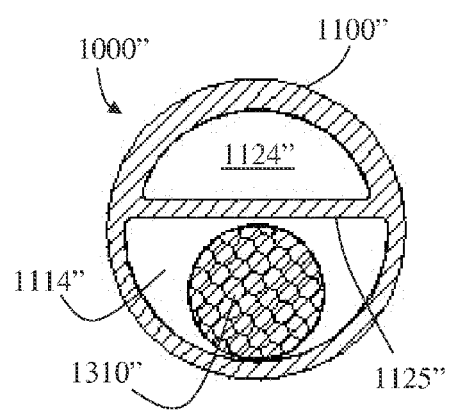

In some embodiments, the second minimal cross section is sized and shaped such that guide wire 1310 can be selectively fit, snugly, in the second minimal cross section in order to achieve blocking of distal opening 1118 and/or second segment 1330 distal to lateral infusion opening 1116. In some embodiments, the second minimal cross section is circular whereas the first minimal cross section is sized and shaped to virtually enclose a circle with identical dimensions to said second minimal cross section (as shown in the shape difference of infusion lumen 1114 in FIG. 1B vs. FIG. 1C). The first minimal cross section may be of any shape such as circular, elliptic or crescent. FIGS. 4A-B schematically illustrate cross sections of two other possible exemplary catheter portions 1000' and 1000" which comprise combined infusion-guidewire lumens 1114' and 1114", respectively. Both catheters 1000' and 1000" are over-the-wire type balloon catheters. In FIG. 4A, an inner wall 1125' dividing between infusion lumen 1114' and inflation lumen 1124' is partially curved to allow partial nesting with part of a guide wire 1310' periphery in contact. Other part of guide wire periphery not in contact with inner wall 1125' is opened at least partially to infusion lumen 1114' interior so that fluid passing in the lumen may contact it. FIG. 4B shows infusion lumen 1114" and inflation lumen 1124" divided with a straight inner wall 1125", while guide wire 1310" is mostly opened to infusion lumen 1114" interior and may be only tangential to inner wall 1125".

In an aspect of some embodiments, a method is disclosed for operating a balloon catheter, such as balloon catheter 1000, according to the present disclosure, comprising at least one of the following steps (not necessarily in same order):

1. inserting guidewire 1310 in a luminal vessel, such as a vein or an artery, optionally a coronary, a peripheral or dialysis target vessel;
2. delivering balloon catheter 1000 in the luminal vessel over guidewire 1310 to a chosen target;
3. inflating inflatable member 1200 to occlude, at least partially, the luminal vessel at the target;
4. infusing a fluid (e.g., a liquid or suspended medicament or contrast enhancing medium) through lateral infusion opening 1116 such that minimal or no fluid passes beyond inflatable member 1200.

In some embodiments, steps 3 and 4 are performed simultaneously and/or in overlap. In some embodiments, guide wire 1310 is selectively occupying or withdrawn from second segment 1330 in infusion lumen 1114 according to need. In some embodiments, catheter 1000 first engages guide wire 1310 by inserting it via distal opening 1118, or alternatively, by inserting guide wire 1310 in infusion lumen 1114 via proximal opening 1112. In some embodiments, the infusing occurs while the inflatable member is filled and/or expanded, optionally fully or partially. Optionally, the inflatable member is deflated after the infusing. In some embodiments, the inflating generates a dilatation force in a magnitude above a mechanical yield point of a stenotic blood vessel wall. Optionally, alternatively or additionally, the mechanical interaction between the filled and/or expanded inflatable member with the blood vessel portion in contact creates a sealing thus obstructing and/or diminishing substantially a fluid passing therebetween.

In different exemplary embodiments, a valving mechanism may include an additional valve or a seal for sealing around a guide wire passing therethrough, and/or selectively seal an opening or a segment of an infusion lumen when the guide wire is removed or otherwise absent. In some embodiments, a catheter includes at least one one-way valve allowing a guide wire passing therethough while sealing fluid passage. Optionally, the one-way valve is disposed adjacent to catheter's distal end and/or between a distal opening and a lateral infusion opening in the infusion lumen. Optionally, alternatively or additionally, the one-way valve is disposed adjacent to catheter's proximal end and/or between a proximal opening and a lateral infusion opening in the infusion lumen. Optionally, the catheter and/or the valving mechanism includes a septum seal.

Figure 2A:
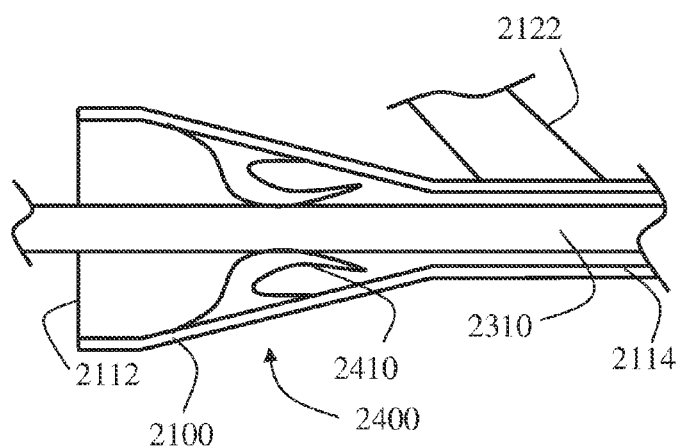
FIGS. 2A-B schematically illustrate portions in cross section of an exemplary balloon catheter and seals provided therein, in accordance with embodiments of the present invention.
Figure 2B:
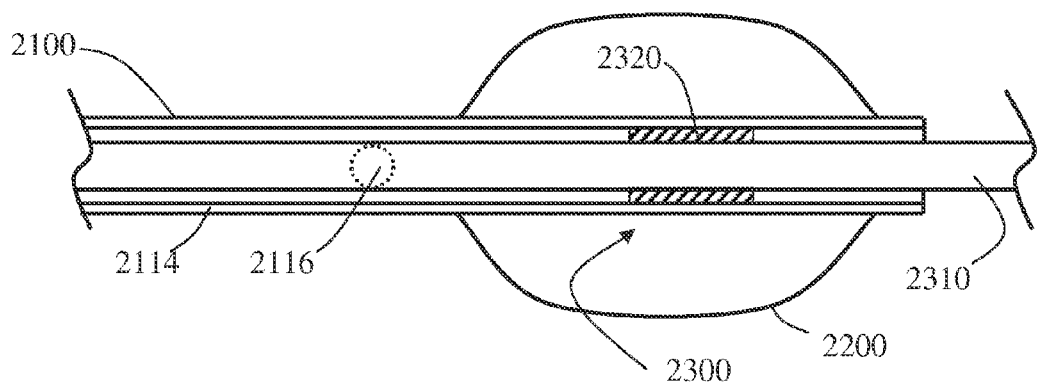

FIGS. 2A-B schematically illustrate portions in cross section of an exemplary balloon catheter 2000 and seals provided therein. Optionally and alternatively, only one seal of FIG. 2A or FIG. 2B is provided therein. FIG. 2A shows a proximal portion of balloon catheter 2000, comprising a wall 2100 enclosing an infusion lumen 2114 openable at proximal infusion inlet or port 2112 to an infusion fluid source (not shown), as well as an inflation lumen (not shown) openable to proximal inflation port 2122. As shown, a guide wire 2310 is passable through infusion lumen 2114 and proximal infusion port 2112 and therefore a proximal valving mechanism 2400 is required to avoid backflow via proximal infusion port 2112. In some embodiments, proximal valving mechanism 2400 includes a proximal seal 2410 in the form of a "wire seal" adapted to maintain sealing around periphery of guide wire 2310, if present as shown. As such, proximal seal 2410 may include a plurality of overlapping seal segments adapted to extend or narrow against outer periphery of the guide wire while maintaining sealing. In some embodiments, proximal valving mechanism 2400 may also include a zero seal (which is "normally sealing"), in addition to the wire seal, not shown, adapted to seal fluid backflow through proximal infusion valve port 2112 when a wire is absent.

FIG. 2B shows a distal portion of balloon catheter 2000 in which an inflatable member (balloon 2200) is fixated thereto. Infusion lumen 2114 is opened to outer environment with a lateral infusion opening 2116. Distally to lateral infusion opening 2116 in infusion lumen 2114 there is provided a proximal valving mechanism 2300 comprising a septum seal 2320, optionally made of a highly elastic and/or a viscoelastic material, allowing distal sealing either if guide wire 2310 is absent (not shown) or passes therethrough (as shown).

Figure 3A:
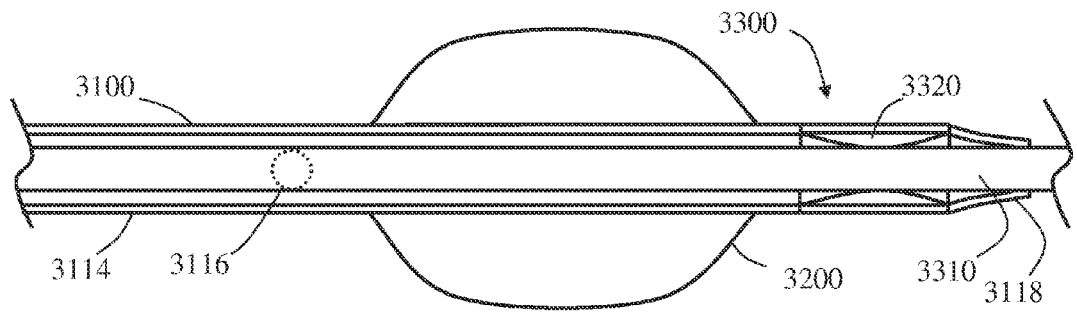
FIGS. 3A-B schematically illustrate portions in cross section of a different exemplary balloon catheter and seals provided therein, in accordance with embodiments of the present invention.
Figure 3B:
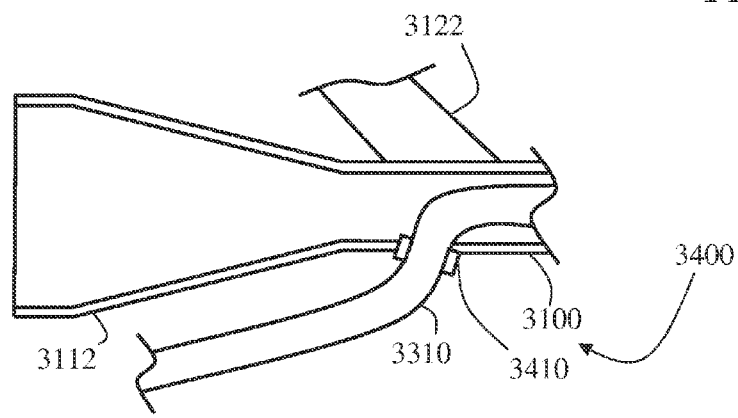

FIGS. 3A-B schematically illustrate portions in cross section of a different exemplary balloon catheter 3000 and optional exemplary seals provided therein. Balloon catheter 3000 includes a wall 3100 enclosing an infusion lumen 3114 openable at a proximal infusion inlet port 3112 to an infusion fluid source (not shown), as well as an inflation lumen (not shown) openable to proximal inflation port 3122. An inflatable member (balloon 3200) is fixated at distal portion of catheter 3000. As shown, guide wire 3310 is passable through infusion lumen 3114 however it does not pass through proximal infusion port 3112 but rather through a dedicated guide wire port 3130. Therefore a proximal valving mechanism 3400 comprising an O-ring or a septum seal 3410, is used in guide wire port 3130 in order to avoid backflow of infusion fluid therethrough. In the distal portion of balloon catheter 3000, as shown in FIG. 3B, infusion lumen 3114 is shown opened to outer environment with a lateral infusion outlet or opening 3116. Distally to lateral infusion opening 3116 in infusion lumen 3114 there is provided a distal valving mechanism 3300 comprising a normally closed seal 3320 adapted to maintain sealing therethrough to infusion fluids either if guide wire 3310 passes therethrough or is absent. In some embodiment, seal 3320 is an inflatable doughnut shaped, optionally continuously pressurized, so that it maintains a minimal sized core opening changeable from zero (when guide wire 3310 is absent) to outer diameter of guidewire 3310 if it passes therethrough.

In some embodiments, balloon catheter 3000 ends distally with a soft, elastic and/or pliable descending conic member 3118 which is normally tapered with a distal inner diameter substantially smaller than its proximal inner diameter at least at non-stressed and/or non-stretched form. If stretched out, for example in case a guide wire passes therethrough and having dimensions greater than those imposed by the non-stretched conic member 3118, it maintains a sealed distal end around outer boundaries of conic member 3118. Such sealing function may achieve at least one of: blocking fluid therethough from infusion lumen to our environment of any infusion fluid such as saline or medicament, and/or blocking fluid travel therethrough from outer environment and into infusion lumen of body fluid such as blood. In some embodiments, conic member 3118 is designed, sized and/or configured such that guide wires having outer diameters between 0.01" to 0.2", optionally 0.018" to 0.035" or higher or lower or intermediate, are unhinderly passable therethrough, and optionally also stretching it at least partially to a radially extended form. In some embodiments, conic member 3118 is normally sealed so that in absence of any wire extending therethrough it is fully compressed and sealed to fluids, at least at its distal-most portion.

Reference is made to FIGS. 5A-H which schematically illustrate cross sections in portions of different exemplary catheters, in accordance with embodiments of the present invention. All these cross sections represent portions of corresponding infusion lumens, each extending between a distal fluid inlet and a proximal fluid outlet. FIG. 5A shows a portion 3510 having a circular cross section with a wall 3511 enclosing a first infusion lumen 3512 with a dedicated area 3513 for partial nesting of a guidewire (not shown) shaped to enclose most of guidewire's periphery, and a second inflation lumen 3514. Optionally, portion 3510 is of a 5.5 French (F) PTA catheter whereas infusion lumen 3512 area is about 1.2 mm$^2$ and inflation lumen 3514 area is about 0.34 mm$^2$ FIG. 5B shows a portion 3520 having a circular cross section with a wall 3521 enclosing a first infusion lumen 3522 with a dedicated area 3523 for partial nesting of a guidewire (not shown) shaped to enclose approximately half of guidewire's periphery, and a second inflation lumen 3524. Optionally, portion 3520 is of a 5.5 F PTA catheter whereas infusion lumen 3522 area is about 1.28 mm$^2$ and inflation lumen 3524 area is about 0.31 mm$^2$ FIG. 5C shows a portion 3530 having a circular cross section with a wall 3531 enclosing a first infusion lumen 3532 with a dedicated area 3533 for partial nesting of a guidewire (not shown) shaped to enclose most of guidewire's periphery, and a second inflation lumen 3534. Optionally, portion 3530 is of a 5 F occlusion balloon catheter whereas infusion lumen 3532 area is about 0.82 mm$^2$ and inflation lumen 3514 area is about 0.54 mm$^2$ FIG. 5D shows a portion 3540 having a circular cross section with a wall 3541 enclosing a first infusion lumen 3542 with a dedicated area 3543 for partial nesting of a guidewire (not shown) shaped to enclose approximately half of guidewire's periphery, and a second inflation lumen 3544. Optionally, portion 3540 is of a 6 F PTA catheter whereas infusion lumen 3542 area is about 1.52 mm$^2$ and inflation lumen 3444 area is about 0.5 mm$^2$ FIG. 5E shows a portion 3550 having a circular cross section with a wall 3551 enclosing a first infusion lumen 3552 with a dedicated area 3553 for partial nesting of a guidewire (not shown) shaped to enclose most of guidewire's periphery, and a second inflation lumen 3554. Optionally, portion 3550 is of a 5 F occlusion balloon catheter whereas infusion lumen 3552 area is about 1.09 mm$^2$ and inflation lumen 3554 area is about 0.27 mm$^2$ FIG. 5F shows a portion 3560 having a circular cross section with a wall 3561 enclosing a first infusion lumen 3562 with a dedicated area 3563 for partial nesting of a guidewire (not shown) shaped to enclose most of guidewire's periphery, and a second inflation lumen 3564. Optionally, portion 3560 is of a 6 F PTA catheter whereas infusion lumen 3562 area is about 1.48 mm$^2$ and inflation lumen 3564 area is about 0.69 mm$^2$ FIG. 5G shows a portion 3570 having a circular cross section with a wall 3571 enclosing a first infusion lumen 3572, a second guidewire lumen 3573 and a third inflation lumen 3574. Optionally, portion 3570 is of a 5.5 F PTA catheter whereas infusion lumen 3572 area is about 0.49 mm$^2$, guidewire lumen 3573 area is about 0.69 mm$^2$ and inflation lumen 3574 area is about 0.35 mm$^2$ FIG. 5H shows a portion 3580 having a circular cross section with a wall 3581 enclosing a first infusion lumen 3582 with enough space yet without a dedicated area for partial nesting of a guidewire (not shown), and a second inflation lumen 3583. Optionally, portion 3580 is of a 5.5 F PTA catheter whereas infusion lumen 3582 area is about 1.49 mm$^2$ and inflation lumen 3583 area is about 0.27 mm$^2$.

Reference is now made to FIGS. 6A-B which schematically illustrate an exemplary infusion lumen 110IL, as part of a catheter, comprising a first exemplary valving mechanism, in accordance with embodiments of the present invention. The catheter includes an infusion wall 110 enclosing infusion lumen 110IL that extends axially therealong. Infusion wall includes a proximal wall segment 115, a distal wall segment 113 and an intermediate wall segment 111 extending therebetween. Proximal wall segment 115 comprises a proximal guidewire opening 118 and distal wall segment 113 comprises a distal guidewire opening 119. A guidewire 120 is shown extending through infusion lumen 110IL having its distal part provided through distal guidewire opening 119 and its proximal part provided through proximal guidewire opening 118. During treatment, including catheter delivery, deployment or withdrawal, guidewire 120 may pass into infusion lumen 110IL through proximal guidewire opening 118 or through distal guidewire opening 119.

Proximal wall segment 115 adjoins intermediate wall segment 111 with a widening 114, and intermediate wall segment 111 adjoins distal wall segment 113 with a narrowing 112. Widening 114 and/or narrowing 112 may be gradual or steep.

Intermediate wall segment 111 includes a fluid inlet 116 appositional to proximal wall segment 115 and a fluid outlet 117 appositional to distal wall segment 113.

Infusion lumen 110IL is shown during fluid dispersion when fluid inlet 116 is located outside a patient body and fluid outlet 117 is located inside the patient body in a specific location in a bodily lumen, optionally a blood vessel such as a vein or an artery, optionally in apposition to a lesion or a stenosis. A fluid inlet flow rate $F_{in}$ travels in infusion lumen 110IL through fluid inlet 116 while a fluid outlet flow rate $F_{out}^1$ travels out of infusion lumen 110IL to a target location inside patient's body through fluid outlet 117.

In some embodiments, infusion lumen 110IL in distal wall segment 113 is sized, shaped, and/or inner surface of distal wall segment 113 is textured, such, to build a distal pressure gradient allocating a distal flow rate $F_{out}^3$ through distal guidewire opening 119, being 40% or less fluid outlet flow rate $F_{out}^1$ through fluid outlet 117, optionally 20% or less, optionally 10% or less, optionally 5% or less, optionally, 2% or less, or higher, or lower, optionally null, or an intermediate percentage; optionally when distal wall segment 113 is unobstructed, such as with guidewire 120, or optionally when distal wall segment 113 is obstructed with guidewire 120.

In some embodiments, infusion lumen 110IL in proximal wall segment 115 is sized, shaped, and/or inner surface of proximal wall segment 115 is textured, such, to build a distal pressure gradient allocating a negative flow rate $F_{out}^2$ through proximal guidewire opening 118, being 40% or less fluid outlet flow rate $F_{out}^1$ through fluid outlet 117, optionally 20% or less, optionally 10% or less, optionally 5% or less, optionally, 2% or less, or higher, or lower, optionally null, or an intermediate percentage; optionally when proximal wall segment 115 is unobstructed, such as with guidewire 120, or optionally when proximal wall segment 115 is obstructed with guidewire 120.

Optionally, guidewire 120 is a 0.035" guidewire, or a 0.025" guidewire, or a 0.018" guidewire, or a 0.014" guidewire, or lower, or higher, or intermediate in size.

Distal pressure gradient and/or proximal pressure gradient is optionally determined according to an infusion fluid viscosity of at least 0.65 centipoises ("cP"), or optionally of at least 3 cP, or optionally at least 6 cP, or optionally at least 8 cP; considering that water viscosity at a temperature of 37° C. is approximately 0.69 cP, blood viscosity at same temperature is approximately 3 to 4 cP, and iodine based contrast media is commonly between approximately 4 cP to approximately 12 cP.

In some embodiments, a cross section area of fluid outlet 117 $D_{prx}$ divided by a cross section area A of distal guidewire opening 119 is at least 1.5, optionally at least 2, optionally at least 3, optionally at least 5, optionally at least 10, or higher, or lower, or an intermediate value. Optionally, a cross section area $D_{gw}$ of proximal guidewire opening 118 is equal to or less than cross section area A distal guidewire opening 119.

Optionally, a cross section of infusion lumen 110IL in distal wall segment 113 and/or in proximal wall segment 115 is circular and 0.3 mm to 1.5 mm in diameter.

In some embodiments, proximal wall segment 115 and/or distal wall segment 113 is at least 10 mm in length, optionally at least 20 mm, optionally at least 50 mm, optionally at least 100 mm, or higher, or lower, or has an intermediate value.

In some embodiments, distal guidewire opening 119 and/or proximal guidewire opening 118 is 0.3 mm to 2 mm in diameter, optionally 0.5 mm to 1.5 mm, optionally 0.9 to 1 mm, or optionally 0.3 mm to 0.9 mm, or optionally about 0.95 mm.

Infusion lumen 110IL at intermediate wall segment 111 may take any of a plurality of cross sections forms, as long as they are sized and shaped to virtually enclose a circle with dimensions equal or higher than to outer dimensions of guidewire 120 or a thicker guidewire that can be used with the catheter. FIGS. 11A-C schematically illustrate different exemplary cross section shapes for of infusion lumen 110IL at intermediate wall segment 111, in accordance with embodiments of the present invention. FIG. 11A shows a circular cross section of intermediate wall segment 111 with internal diameter ID equal or greater than guidewire 120 diameter. FIG. 11B shows a cross section of infusion lumen 110IL at intermediate wall segment 111 being noncircular shaped with a smallest distance APL between antipodal points AP1 and AP2 at an inner boundary thereof. FIG. 11C shows a cross section of infusion lumen 110IL at intermediate wall segment 111 being crescent shaped with a smallest distance ARL between two opposing arcs AR1 and AR2 at an inner boundary thereof. Optionally distance APL and/or ARL is at least 0.3 mm, optionally at least 0.5 mm, optionally at least 0.9 mm, optionally at least 1.5 mm, optionally at least 3 mm, or higher, or lower, or an intermediate value. In some embodiments, the cross section area of infusion lumen 110IL at intermediate wall segment 111, regardless of any chosen shape (as in FIGS. 11A-C or otherwise) is at least 1 mm2, optionally 1.5 mm², optionally at least 1.75 mm², optionally at least 2 mm², optionally at least 4 mm², or higher, or lower, or of any intermediate value.

Fluid outlet 117 may include any number of openings of any form and size, and of any arrangement with any pattern. As such, fluid outlet may include at least one hole (i.e. a through opening), at least one slit and/or at least one pressure sensitive opening. Optionally the at least one slit is configured to open above a predetermined infusion pressure, optionally of at least 1 bar, optionally at least 2 bar, optionally at least 4 bar, or higher, or lower, or intermediate. Optionally, there are at least 2 openings, optionally at least 4 openings, optionally at least 10 openings, optionally at least 50 openings, or higher, or lower, or an intermediate number. In some embodiments, the overall area of fluid outlet 117 is equal or higher than cross section area (minimal or average, in case it is not constant) of infusion lumen 110IL at intermediate wall segment 111, optionally equal or higher than 1.5 times its size, optionally equal or higher than 2 times its size, optionally equal or higher than 5 times its size, or higher, or lower, or an intermediate value. Optionally and alternatively, the overall area of fluid outlet 117 is equal or higher than cross section area of infusion lumen 110IL at intermediate wall segment 111 less cross section area of guidewire 120. In some embodiments, fluid outlet 117 may include a number of openings, optionally provided in form of series, optionally around a periphery of the catheter and/or along a portion of its length. At least one opening may be directly opposing an at least one opening at an opposing wall portion of the catheter, and/or at least one opening may be peripherally and/or longitudinally offset to another at least one opening at a different wall portion of the catheter. FIGS. 12A-C schematically illustrate different exemplary fluid outlet types and/or distribution, in accordance with embodiments of the present invention. FIG. 12A shows infusion lumen 110IL at intermediate wall segment 111 with a crescent cross section and a single hole as fluid outlet 117. FIG. 12B shows infusion lumen 110IL at intermediate wall segment 111 with a crescent cross section and a number of holes as fluid outlet 117. FIG. 12C shows infusion lumen 110IL at intermediate wall segment 111 with a crescent cross section and a single pressure sensitive slit as fluid outlet 117.

In some embodiments the catheter also comprises an inflatable member and an inflation wall enclosing an inflation lumen with the infusion wall along a length thereof. The inflatable member may be a dilatation balloon comprising a non-compliant or a semi-compliant material, or it may be an occlusion balloon comprising a compliant material. FIGS. 7A-B schematically illustrate balloon catheter incorporating exemplary valving mechanisms differentiated by balloon location relative to fluid outlet, in accordance with embodiments of the present invention. FIG. 7A shows a catheter 100 which includes infusion wall 110 enclosing infusion lumen 110IL, similar to as described above. Catheter 100 also includes an inflatable member 136 and an inflation wall 130 enclosing an inflation lumen 130IL with infusion wall 110 along part of inflation lumen length. Inflation lumen 130IL includes an inflation inlet 132, optionally located in relative opposition to proximal guidewire opening 118 and/or to fluid inlet 116, as well as an inflation outlet 134 located within the sealed inner boundary of inflatable member 136. Inflatable member may be configured as a dilatation and/or occlusion balloon. As shown, in this example, dilatation member 136 is provided in between fluid outlet 117 and distal guidewire opening 119. This will allow dispersion of fluid such as contrast enhancing media, flushing fluid, dissolvent and/or medicament only proximal and optionally adjacent to inflatable member 136.

FIG. 7B shows a catheter 140 which includes infusion wall 110 enclosing infusion lumen 110IL, similar to as described above. Catheter 140 also includes an inflatable member 136 and an inflation wall 130 enclosing an inflation lumen 130IL with infusion wall 110 along part of inflation lumen length. Inflation lumen 130IL includes an inflation inlet 132, optionally located in relative opposition to proximal guidewire opening 118 and/or to fluid inlet 116, as well as an inflation outlet 134 located within the sealed inner boundary of inflatable member 136. Inflatable member may be configured as a dilatation and/or occlusion balloon. As shown, in this example, fluid outlet 117 includes a proximal-most opening 142 and a distal-most opening 144, wherein inflatable member 136 extends therebetween. This will allow dispersion of fluid such as contrast enhancing media, flushing fluid, dissolvent and/or medicament proximally and distally, and optionally adjacent, to inflatable member 136.

In some embodiments other valving or sealing means are provided in addition to the guidewire based valving mechanism in order to improve and/or offer different possibilities for delivering fluids into a target bodily lumen. FIGS. 8A-B schematically illustrate an exemplary infusion lumen 210IL, as part of a catheter, comprising an exemplary valving mechanism with additional backflow seal, in accordance with embodiments of the present invention. The catheter includes an infusion wall 210 enclosing infusion lumen 210IL that extends axially therealong. Infusion wall includes a proximal wall segment 215, a distal wall segment 213 and an intermediate wall segment 211 extending therebetween. Proximal wall segment 215 comprises a proximal guidewire opening 218 and distal wall segment 213 comprises a distal guidewire opening 219. A guidewire 220 is shown extending through infusion lumen 210IL having its distal part provided through distal guidewire opening 219 and its proximal part provided through proximal guidewire opening 218. During treatment, including catheter delivery, deployment or withdrawal, guidewire 220 may pass into infusion lumen 210IL through proximal guidewire opening 218 or through distal guidewire opening 219.

Proximal wall segment 215 adjoins intermediate wall segment 211 with a widening 214, and intermediate wall segment 211 adjoins distal wall segment 213 with a narrowing 212. Widening 214 and/or narrowing 212 may be gradual or steep.

Intermediate wall segment 211 includes a fluid inlet 216 appositional to proximal wall segment 215 and a fluid outlet 217 appositional to distal wall segment 213.

As shown, a guidewire seal 230 is provided in infusion lumen 210IL between fluid inlet 216 and proximal guidewire opening 218. In some embodiments, guidewire seal 230 is an inflatable annular seal which includes an annular inflatable body 231 having a lumen 232, and a seal inlet 234. In some embodiments, inflatable body 231 has an outer periphery, fixed to infusion wall 210, and an inner periphery surrounding lumen 232 with a selectively changeable inner diameter. In some embodiments, seal inlet 234 is provided adjacent and in direct fluid communication with fluid inlet 216, optionally dividing an intake passage at fluid inlet 216 to seal inlet 234 and to an infusion inlet 233, so that when fluid is forced through fluid inlet 216 it will be divided between filling infusion lumen 210IL and fluid delivery through fluid outlet 217, and inflating guidewire seal 230 such that its lumen 232 decreases in diameter down to a minimal degree. In some embodiments, guidewire seal 230 may decrease in inner diameter below to a predetermined guidewire diameter. When guidewire seal 230 is deflated its lumen 232 is relatively enlarged so that guidewire 220 can travel freely therethrough (as shown in FIG. 8A) whereas when it is inflated to a certain degree, optionally up to a maximal inflation volume, lumen 232 decreases in diameter to equal or less than guidewire 220 outer boundaries (as shown in FIG. 8B) therefore sealing a fluid passage therebetween. In some embodiments, inflatable body 231 includes a compliant material capable of conforming to guidewire boundaries at certain inner pressures.

FIGS. 9A-B schematically illustrate an exemplary infusion lumen 310IL, as part of a catheter, comprising an exemplary valving mechanism with additional exemplary proximal and distal sealing sets, in accordance with embodiments of the present invention. The catheter includes an infusion wall 310 enclosing infusion lumen 310IL that extends axially therealong. Infusion wall includes a proximal wall segment 315, a distal wall segment 313 and an intermediate wall segment 311 extending therebetween.

Proximal wall segment 315 comprises a proximal guidewire opening 318 and distal wall segment 313 comprises a distal guidewire opening 319. A guidewire 320 is shown extending through infusion lumen 310IL having its distal part provided through distal guidewire opening 319 and its proximal part provided through proximal guidewire opening 318. During treatment, including catheter delivery, deployment or withdrawal, guidewire 320 may pass into infusion lumen 310IL through proximal guidewire opening 318 or through distal guidewire opening 319.

Proximal wall segment 315 adjoins intermediate wall segment 311 with a widening 314, and intermediate wall segment 311 adjoins distal wall segment 213 with a narrowing 312. Widening 314 and/or narrowing 312 may be gradual or steep.

Intermediate wall segment 311 includes a fluid inlet 316 appositional to proximal wall segment 315 and a fluid outlet 317 appositional to distal wall segment 313.

As shown, a proximal guidewire seal 330 is provided in infusion lumen 310IL between fluid inlet 316 and proximal guidewire opening 318. In some embodiments, proximal guidewire seal 330 is an inflatable annular seal which includes an annular inflatable body 331 having a lumen 332, and a seal inlet 334. In some embodiments, inflatable body 331 has an outer periphery, fixed to infusion wall 310, and an inner periphery surrounding lumen 332 with a selectively changeable inner diameter. In some embodiments, seal inlet 334 is provided adjacent and in direct fluid communication with fluid inlet 316, optionally dividing an intake passage at fluid inlet 316 to seal inlet 334 and to an infusion inlet 333, so that when fluid is forced through fluid inlet 316 it will be divided between filling infusion lumen 310IL and fluid delivery through fluid outlet 317, and inflating proximal guidewire seal 330 such that its lumen 332 decreases in diameter down to a minimal degree.

A distal guidewire seal 340 is also provided in infusion lumen 310IL between fluid outlet 317 and distal guidewire opening 319. In some embodiments, distal guidewire seal 340 is an inflatable annular seal which includes an annular inflatable body 341 having a lumen 342, and a seal inlet 344. In some embodiments, inflatable body 341 has an outer periphery, fixed to infusion wall 310, and an inner periphery surrounding lumen 342 with a selectively changeable inner diameter. In some embodiments, seal inlet 334 is provided in infusion lumen 310IL so that when pressure arises therein, fluid is forced through fluid outlet 317 in parallel or after to inflating distal guidewire seal 340 such that its lumen 342 decreases in diameter down to a minimal degree.

In some embodiments, proximal guidewire seal 330 and distal guidewire seal 340 may decrease in inner diameter below to a predetermined guidewire diameter. When guidewire seals 330 and 340 deflates, their lumens 332 and 342, respectively, are relatively enlarged so that guidewire 320 can travel freely therethrough whereas when they are inflated to a certain degree, optionally up to a maximal inflation volume, lumens 332 and 342 decrease in diameter to equal or less than guidewire 320 outer boundaries (as shown in FIG. 9B) therefore sealing a fluid passage therebetween. In some embodiments, inflatable bodies 331 and 341 include compliant material capable of conforming to guidewire boundaries at certain inner pressures.

In some embodiments, a proximal zero seal 352 is provided between fluid inlet 316 and proximal guidewire opening 318. Optionally and additionally, a distal zero seal 354 is provided between fluid outlet 317 and distal guidewire opening 319. Zero seals 352 and 354 are normally closed to fluid flow at the absence of a guidewire passing therethrough. FIG. 9A shows a scenario in which a guidewire is absent from infusion lumen 310IL yet by delivering a fluid $F_{in}$ therein through fluid inlet 316 a fluid $F_{out}$ is delivered out only through fluid outlet 317 and not through guidewire openings 318 and 319 since that zero seals 352 and 354 are closed and sealed to fluid passage therethrough. FIG. 9B shows another scenario in which guidewire 320 travels through infusion lumen 310IL and guidewire openings 318 and 319, forcing zero seals 352 and 354 to open, yet by delivering a fluid $F_{in}$ in infusion lumen 310IL it can only be delivered (as fluid $F_{out}$) through fluid outlet 317 since that both guidewire seals are inflated and seal fluid passage between them and guidewire 320.

Reference is now made to FIGS. 10A-I which illustrate side views and cross section views of an exemplary angioplasty infusion balloon catheter 400 comprising a guidewire based valving mechanism, in accordance with embodiments of the present invention. Balloon catheter 400 includes an elongated shaft 410 connected at its proximal end with a triple connector 420. An inflatable angioplasty balloon 430 is provided along a portion of its distal end. Shaft 410 encloses an infusion lumen 414 and an inflation lumen 415 separated and sealed to infusion lumen 414 with a wall 413. Infusion lumen 414 extends along entire length and opened at both ends of catheter 400, having a proximal guidewire opening 422 and a distal guidewire opening 424, allowing in size and shape passage in between and therethrough of a guidewire 440. Infusion lumen 414 also includes a fluid inlet 421 in triple connector 420 distally to proximal guidewire opening 422. Fluid inlet 421 comprises a single opening and connection means (optionally a luer connection to a syringe) for allowing selective introduction into infusion lumen 414 of at least type of fluid, such as a contrast enhancing medium, flushing fluid (e.g., saline), medicament, chemical or biological compounds, or others. A fluid outlet 412 is provided proximally and close (optionally adjacent) to balloon 430 and allows delivery of fluid outside infusion lumen 414 proximally and adjacent to balloon 430. Fluid outlet 412 may include a single opening (as shown) or a plurality of openings of any chosen number, form, arrangement or other.

Inflation lumen 415 extends about most of infusion lumen 414 length, between an inflation inlet 423 in triple connector 420, distally to proximal guidewire opening 422 and in general opposite direction to fluid inlet 421, and an inflation outlet opened to inner volume of balloon 430. Inflation inlet 423 comprises a single opening and connection means (optionally a luer connection to a syringe) for allowing selective delivery into or withdrawal from inflation lumen 415 of inflation fluid (optionally saline, optionally with contrast enhancing agent) for inflating and deflating, respectively, balloon 430.

Infusion lumen 414 includes a proximal segment 409 extending at least partially between proximal guidewire opening 422 and fluid inlet 421, a distal segment 418 extending at least partially between fluid outlet 412 and distal guidewire opening 424, and an intermediate segment extending in between proximal segment 409 and distal segment 418. Proximal segment 409 and distal segment 418 have circular cross sections equal or slightly over cross section of guidewire 440 so that the guidewire can snugly fit therein yet can be passed freely either proximally or distally. The intermediate segment of infusion lumen 414 has a crescent shaped cross section which encloses a circular area equal or greater than cross section area of guidewire 440. This way, a fluid can travel freely in infusion lumen 414 intermediate segment from fluid inlet 421 to fluid outlet 412 despite presence of guidewire 440. Proximal segment 409 adjoins the intermediate segment with a gradual widening 419 and the intermediate segment adjoins distal segment 418 with a gradual narrowing 417. The close fit of guidewire 440 in proximal segment 409 and distal segment 418 of infusion lumen 414 and substantial lengths thereof (greater than 20 mm, optionally about 50 mm, each) seals (fully or partially) fluid travel therethrough, so that most or all infusion fluid entering infusion lumen 414 through fluid inlet 421 will be delivered through fluid outlet 412 and not through proximal guidewire opening 422 and distal guidewire opening 424, at least as long as guidewire 440 nests therein and obstructs them.

Balloon 430 includes a non-compliant or semi-compliant inflatable membrane 431 fixated in both ends to shaft 410 outer periphery with a proximal constriction 432 and a distal constriction 433. An optional soft tip 434 is provided for improving safety to vasculature during delivery. Balloon 430 is configured for dilating a narrowed portion, optionally stenotic, of a blood vessel by inflating it under a moderate to high pressure, according to anatomic location and blood vessel diameter at the treatment location. Inflation lumen 415 being completely sealed to infusion lumen 414 allows an independent applicability of balloon 430 with respect to infusion and fluid delivery through fluid outlet 412, so that fluid can be delivered if balloon 430 is inflated, deflated or while being in a process of inflation or deflation. Delivering contrast media, agent or medicament proximally to balloon 430 when inflated has some advantages as balloon 430 acts also as an occlusion balloon enabling this way a localized delivery and treatment instead of systemic.

In some embodiments of the present invention, a fluid outlet of a dilatation balloon catheter has a single, substantially large opening. In some embodiments, the total opened area of the opening is equal to or greater than a minimal cross section area of the infusion lumen, in a portion proximal to the opening. Optionally and alternatively, the total opened area is equal or greater than a minimal cross section area of the infusion lumen, in a portion proximal to the opening less a cross section area of a guidewire of a minimally allowed diameter, or of a maximally allowed diameter, or an intermediate value. In some embodiments, total opened area of fluid outlet is at least 0.5 mm$^2$, optionally at least 1 mm$^2$, optionally at least 2 mm$^2$, optionally at least 5 mm$^2$, optionally about 1.2 mm$^2$, optionally about 2.5 mm$^2$ or higher, or lower, or an intermediate value. One advantage of a substantially large single opening, rather than a plurality of smaller openings, is the possibility to inject fluids in equal or greater rates without causing jets from the fluid outlet. In some embodiments, in order to prevent a possible deformation (e.g., a kinking, a bending, a twisting, or a combination thereof, or other) and/or deterioration the catheter shaft adjacent the opening, due to the possible increased weakening made by a substantially large single opening, a structural fortification is added to the catheter shaft about the opening. FIGS. 13, 14 and 15 disclose three exemplary types of fortifications.

The device illustrated in FIGS. 10A-10I is made according to the principles illustrated schematically in FIG. 7A. As noted above, it is advantageous for the lengths of the narrowed portions of the infusion lumen at the proximal and distal portions of the catheter (designated 113 and 115 in FIG. 7A) to be 20 mm long or more, and also for the infusion opening positioned proximal to the balloon (designated 117 in FIG. 7A) to be a single opening having a cross sectional area equal to or greater than the minimal cross sectional area of the infusion lumen in between the narrowed portions minus the cross sectional area of the largest diameter allowed guidewire. The cross sectional area of the largest diameter allowed guidewire is approximately equal to the cross sectional area of at least the distal narrowed portion of the infusion lumen. The cross sectional area of the infusion opening can thus be expressed as equal to or greater than the minimal cross sectional area of the larger cross section portion of the infusion lumen between the narrowed portions (designated 111 in FIG. 7A), and the minimal cross sectional area of the distal narrowed portion of the infusion lumen. This implementation has the significant advantage that the relatively long lengths of the narrowed portions of the infusion lumen substantially seal the ends of the infusion lumen in the presence of the guidewire without the use of additional valving or clamping structures that complicate device construction, and the relatively large infusion opening provides a high volume outflow of infusate. This remains true even when the nesting of the guidewire in the narrowed portions of the infusion lumen is loose enough to allow easy sliding of the catheter structure over the guidewire.

FIGS. 13A-B schematically illustrate cut views of an exemplary balloon catheter 500 with a single proximal fluid outlet 512 comprising a first exemplary fortification, in accordance with embodiments of the present invention. Balloon catheter 500 shown with its distal end includes an elongated shaft 510 and an inflatable angioplasty balloon 530 that is provided along a portion of its distal end. Shaft 510 encloses an infusion lumen 514 and an inflation lumen 515 separated and sealed to infusion lumen 514 with a wall 513. Inflation lumen 515 being completely sealed to infusion lumen 514 allows an independent applicability of balloon 530, so that fluid can be delivered if balloon 530 is inflated, deflated or while being in a process of inflation or deflation.

Infusion lumen 514 includes a distal guidewire opening 524 allowing passage therethrough of a guidewire (not shown) optionally one of several possibly prescribed guidewires. A fluid outlet 512 is provided proximally and close (optionally adjacent) to balloon 530 and allows delivery of fluid outside infusion lumen 514 proximally and adjacent to balloon 530. Infusion lumen 514 narrows with a gradual narrowing 517 into a distal segment 518. Until narrowing 517, infusion lumen 514 has a crescent shaped cross section which encloses a circular area equal or greater than cross section area of a guidewire with a maximally allowed diameter. Distal segment 518 has circular cross sections equal or slightly over cross section of said guidewire so that the guidewire can snugly fit therein yet can be passed freely either proximally or distally. Infusion lumen 514 is configured such that most or all infusion fluid entering therein will be delivered through fluid outlet 512 and not through distal guidewire opening 524, at least as long a prescribed guidewire nests therein and obstructs distal segment 518 and distal guidewire opening 524.

Fluid outlet 512 has a single, substantially large opening with a total opened area being equal to or greater than the cross section area of infusion lumen 514 proximal to fluid outlet 512 less a cross section area of a guidewire with a minimal prescribed diameter. The portion of shaft 510 about fluid outlet 512 is fortified with a mesh patch 545 optionally made from stainless steel in a rectangular shape curved to nest over shaft 510. In some embodiments, the total opened area of fluid outlet 512 is calculated as the total area covered by the outline of fluid outlet 512 less the area covered by mesh 545 above fluid outlet 512. Mesh patch 545 is fixated to shaft 510 with a cover such as a flexible sleeve 540, optionally made from nylon, with a hole cut thereto enclosing fluid outlet 512. Therefore, fluid delivered through fluid outlet 512 will pass then through the portion of mesh insert 545 thereabove and then through the hole in sleeve 540.

FIGS. 14A-B schematically illustrate cut views of an exemplary balloon catheter 600 with a single proximal fluid outlet 612 comprising a second exemplary fortification, in accordance with embodiments of the present invention. Balloon catheter 600 shown with its distal end includes an elongated shaft 610 and an inflatable angioplasty balloon 630 that is provided along a portion of its distal end. Shaft 610 encloses an infusion lumen 614 and an inflation lumen 615 separated and sealed to infusion lumen 614 with a wall 613. Inflation lumen 615 being completely sealed to infusion lumen 614 allows an independent applicability of balloon 630, so that fluid can be delivered if balloon 630 is inflated, deflated or while being in a process of inflation or deflation.

Infusion lumen 614 includes a distal guidewire opening 624 allowing passage therethrough of a guidewire (not shown) optionally one of several possibly prescribed guidewires. A fluid outlet 612 is provided proximally and close (optionally adjacent) to balloon 630 and allows delivery of fluid outside infusion lumen 614 proximally and adjacent to balloon 630. Infusion lumen 614 narrows with a gradual narrowing 617 into a distal segment 618. Until narrowing 617, infusion lumen 614 has a crescent shaped cross section which encloses a circular area equal or greater than cross section area of a guidewire with a maximally allowed diameter. Distal segment 618 has circular cross sections equal or slightly over cross section of said guidewire so that the guidewire can snugly fit therein yet can be passed freely either proximally or distally. Infusion lumen 614 is configured such that most or all infusion fluid entering therein will be delivered through fluid outlet 612 and not through distal guidewire opening 624, at least as long a prescribed guidewire nests therein and obstructs distal segment 618 and distal guidewire opening 624.

Fluid outlet 612 has a single, substantially large opening with a total opened area being equal to or greater than the cross section area of infusion lumen 614 proximal to fluid outlet 612 less a cross section area of a guidewire with a minimal prescribed diameter. The portion of shaft 610 about fluid outlet 612 is fortified with a tube insert 640 optionally made from stainless steel and having an internal diameter equal or greater than a maximally allowed guidewire diameter, and an outer diameter equal or smaller than a circle enclosed in infusion lumen 614 between wall 613 and shaft 610. Tube insert 640 is fixated to shaft 610 optionally by soldering or gluing, or it may be freely disposed therein, optionally in a snug fit. Tube insert 640 includes a hole positioned such to enclose fluid outlet 612. Therefore, fluid delivered through fluid outlet 612 will pass first through the hole in tube insert 640.

FIGS. 15A-B schematically illustrate cut views of an exemplary balloon catheter 700 with a single proximal fluid outlet 712 comprising a third exemplary fortification, in accordance with embodiments of the present invention. Balloon catheter 700 shown with its distal end includes an elongated shaft 710 and an inflatable angioplasty balloon 730 that is provided along a portion of its distal end. Shaft 710 encloses an infusion lumen 714 and an inflation lumen 715 separated and sealed to infusion lumen 714 with a wall 713. Inflation lumen 715 being completely sealed to infusion lumen 714 allows an independent applicability of balloon 730, so that fluid can be delivered if balloon 730 is inflated, deflated or while being in a process of inflation or deflation.

Infusion lumen 714 includes a distal guidewire opening 724 allowing passage therethrough of a guidewire (not shown) optionally one of several possibly prescribed guidewires. A fluid outlet 712 is provided proximally and close (optionally adjacent) to balloon 730 and allows delivery of fluid outside infusion lumen 714 proximally and adjacent to balloon 730. Infusion lumen 714 narrows with a gradual narrowing 717 into a distal segment 718. Until narrowing 717, infusion lumen 714 has a crescent shaped cross section which encloses a circular area equal or greater than cross section area of a guidewire with a maximally allowed diameter. Distal segment 718 has circular cross sections equal or slightly over cross section of said guidewire so that the guidewire can snugly fit therein yet can be passed freely either proximally or distally. Infusion lumen 714 is configured such that most or all infusion fluid entering therein will be delivered through fluid outlet 712 and not through distal guidewire opening 724, at least as long a prescribed guidewire nests therein and obstructs distal segment 718 and distal guidewire opening 724.

Fluid outlet 712 has a single, substantially large opening with a total opened area being equal to or greater than the cross section area of infusion lumen 714 proximal to fluid outlet 712 less a cross section area of a guidewire with a minimal prescribed diameter. The portion of shaft 710 about fluid outlet 712 is fortified with a sheet insert 740 optionally made from stainless steel in a rectangular shape curved to nest in shaft 710. Sheet insert 740 is fixated to shaft 710 optionally by soldering or gluing, or optionally the fortified portion and/or sheet insert 740 is deformed resulting in a tight fit. Tube insert 740 includes a hole positioned such to enclose fluid outlet 712. Therefore, fluid delivered through fluid outlet 712 will pass first through the hole in tube insert 740.

The following table show exemplary not binding parameters for dilatation balloon catheter according to the present invention, separated according to indication (i.e., a specific anatomic location and/or blood vessel type in need for dilatation and/or revascularization).

TABLE 1

Exemplary sizes and indications of balloon catheters

| Indication | Balloon diameter and length (mm) | Catheter length (cm) | Sheath size (F) | Dilatation pressures: nominal and RPB (Atm) | Guidewire size (Inches) |
|---|---|---|---|---|---|
| PTA catheter for treating AV fistula or graft | D: 5-12 L: 20/40/60/80 | 50/80/135 | 6/7/8 | Nom.: 8 RPB: 18-30 | 0.035 |
| PTA catheter for treating large blood vessels | D: 14-18 L: 20/40/60 | 80/120 | 8 | Nom.: 8 RPB: 10-12 | 0.035 |
| PTA catheter for | D: 4-9 | 80/135 | 5-8 | Nom.: 6-8 | 0.018/0.035 |

TABLE 1-continued

Exemplary sizes and indications of balloon catheters

| Indication | Balloon diameter and length (mm) | Catheter length (cm) | Sheath size (F) | Dilatation pressures: nominal and RPB (Atm) | Guidewire size (Inches) |
|---|---|---|---|---|---|
| treating peripheral blood vessels | L: 20-200 | | | RPB: 10-15 | |
| PTA catheter for treating coronary blood vessels | D: 1.5-4<br>L: 8-40 | 140 | 5 | Nom.: 6<br>RPB: 14 | 0.014 |
| Embolectomy catheter | D: 4-15 | 40/80 | 4-8 | | 0.025/0.035 |

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for treating a portion of a blood vessel in a subject, with locally dispersing contrast enhancing material proximally adjacent to the blood vessel portion, the method comprising:
   providing a catheter comprising a shaft including an infusion lumen enclosed within an infusion wall, and an inflation lumen, said inflation lumen is sealed to said infusion lumen and opened to an inflatable member, said infusion lumen is opened with a proximal guidewire opening, a distal guidewire opening, a fluid inlet opening, and a fluid outlet opening;
   inserting a guidewire in the blood vessel;
   delivering said catheter in the blood vessel over said guidewire to a chosen target adjacent to the blood vessel portion, such that said guidewire obstructs a distal wall segment of said infusion wall provided with a narrowing starting distally, and in proximity, to said fluid outlet opening, and extending distally along said distal wall segment towards said distal guidewire opening, wherein said distal wall segment is sized and shaped substantially the same as an external boundary of a correlating portion of the guidewire over at least 10 mm of said infusion wall of said infusion lumen;
   inflating said inflatable member;
   dilating the blood vessel at said chosen target, so as to affect the blood vessel portion;
   occluding the blood vessel at said chosen target; and
   infusing a fluid with the contrast enhancing material as a localized delivery through said fluid outlet opening proximally to said inflatable member.

2. A method according to claim 1, wherein said infusing occurs while the inflatable member is filled with inflation fluid, thereby facilitating said occluding.

3. A method according to claim 1, wherein said infusing is performed before, after, or/and during, said inflating.

4. A method according to claim 1, wherein said inflating facilitates said dilating and said occluding with said inflatable member, and generates a dilatation force in a magnitude above a mechanical yield point of a stenotic blood vessel wall.

5. A method according to claim 1, wherein said infusion wall further comprises a proximal wall segment, and an intermediate wall segment extending between said proximal and distal wall segments, said intermediate wall segment comprises said fluid inlet opening and said fluid outlet opening, and said distal wall segment comprises said distal guidewire opening;
   wherein said intermediate wall segment adjoins said distal wall segment with said narrowing, such that said distal wall segment has a smaller cross sectional area than a cross sectional area of said intermediate wall segment.

6. A method according to claim 5, wherein said smaller cross sectional area of said distal wall segment is sized and shaped for snugly fit of said guidewire.

7. A method according to claim 5, wherein said narrowing extends at least 20 mm in length.

8. A method according to claim 7, wherein said narrowing is constant along said length thereof.

9. A method according to claim 5, wherein said fluid inlet opening is appositional to said proximal wall segment and said fluid outlet opening is appositional to said distal wall segment.

10. A method according to claim 5, wherein said infusion lumen in said distal wall segment is sized, shaped, and/or inner surface of said distal wall is textured, such, to build a distal pressure gradient allocating a distal flow rate through said distal guidewire opening being 20% or less a fluid outlet flow rate through said fluid outlet opening.

11. A method according to claim 5, wherein said proximal wall segment comprises said proximal guidewire opening and adjoins said intermediate wall segment with a widening.

12. A method according to claim 5, wherein said distal wall segment extends along said inflatable member between said fluid outlet opening and said distal guidewire opening.

13. A method according to claim 1, wherein said fluid outlet opening includes a single opening with a total opened area being equal to or greater than the cross section area of infusion lumen proximal to said fluid outlet opening less a cross section area of said guidewire.

14. A method according to claim 1, wherein said infusion wall is provided with a structural fortification about said fluid outlet opening.

15. A method according to claim 1, wherein said catheter includes a valving mechanism, wherein said infusing includes:
   operating said valving mechanism to block said distal opening thereby allowing said infusion fluid to exit mostly or solely through said fluid outlet opening rather than mostly or solely through said distal guidewire opening.

16. A double-lumen balloon catheter for treating a portion of a blood vessel in a subject, and for locally dispersing contrast enhancing material proximally adjacent to the blood vessel portion, the catheter comprising:

a shaft including an infusion lumen, enclosed within an infusion wall, and an inflation lumen, said inflation lumen is sealed to said infusion lumen and opened to an inflatable member, wherein said infusion lumen is opened with a proximal guidewire opening, a distal guidewire opening, a fluid inlet opening and a fluid outlet opening;

wherein said infusion wall comprises a proximal wall segment, a distal wall segment and an intermediate wall segment extending therebetween, said intermediate wall segment comprises said fluid inlet opening and said fluid outlet opening and said distal wall segment comprises said distal guidewire opening;

wherein said intermediate wall segment adjoins said distal wall segment with a narrowing starting distally, and in proximity to, said fluid outlet opening, and extending distally along said distal wall segment, such that said distal wall segment has a smaller cross sectional area than a cross sectional area of said intermediate wall segment;

wherein the catheter is configured for delivering over a guidewire, and wherein said distal wall segment is sized and shaped substantially the same as an external boundary of a correlating portion of said guidewire over at least 10 mm of said infusion wall of said infusion lumen such that said guidewire obstructs said distal wall segment.

17. A double-lumen balloon catheter according to claim 16, wherein said narrowing extends at least 20 mm in length.

18. A double-lumen balloon catheter according to claim 16, wherein said proximal wall segment comprises said proximal guidewire opening and adjoins said intermediate wall segment with a widening.

19. A double-lumen balloon catheter according to claim 16, wherein said narrowing is gradual, such that said intermediate wall segment gradually narrows into said adjoined distal wall segment.

* * * * *